(12) United States Patent
Schmucker-Castner et al.

(10) Patent No.: US 6,897,253 B2
(45) Date of Patent: May 24, 2005

(54) STABLE AQUEOUS SURFACTANT COMPOSITIONS

(75) Inventors: Julie F. Schmucker-Castner, Strongsville, OH (US); Hal Ambuter, Medina, OH (US); Marcia Snyder, Stow, OH (US); Ashley A. Weaver, Arlington, VA (US); Sahira Kotian, Gonzales, LA (US)

(73) Assignee: Noveon IP Holdings Corp., Cleveland, OH (US)

( * ) Notice: Subject to any disclaimer, the term of this patent is extended or adjusted under 35 U.S.C. 154(b) by 122 days.

(21) Appl. No.: 10/602,956

(22) Filed: Jun. 23, 2003

(65) Prior Publication Data

US 2004/0087668 A1 May 6, 2004

Related U.S. Application Data

(62) Division of application No. 09/547,595, filed on Apr. 11, 2000, now Pat. No. 6,635,702.

(51) Int. Cl.$^7$ ................................................ C08K 5/09
(52) U.S. Cl. ........................ 524/291; 524/321; 524/401; 524/548; 524/555; 524/559
(58) Field of Search ................................. 524/291, 321, 524/401, 548, 555, 559

(56) References Cited

U.S. PATENT DOCUMENTS

| | | | |
|---|---|---|---|
| 4,384,974 A | 5/1983 | Guthauser | |
| 4,438,096 A | 3/1984 | Preston | |
| 4,529,773 A | 7/1985 | Witiak et al. | |
| 4,654,207 A | 3/1987 | Preston | |
| 5,011,681 A | 4/1991 | Ciotti et al. | |
| 5,019,376 A | 5/1991 | Uick | |
| 5,230,823 A | 7/1993 | Wise et al. | |
| 5,656,257 A | 8/1997 | Fealy et al. | |
| 5,658,577 A | 8/1997 | Fowler et al. | |
| 5,720,964 A | 2/1998 | Murray | |
| 6,024,946 A | 2/2000 | Dubief et al. | |
| 6,165,454 A | 12/2000 | Patel et al. | |

FOREIGN PATENT DOCUMENTS

| | | |
|---|---|---|
| EP | 0463780 | 1/1996 |
| JP | 4182416 | 6/1992 |
| JP | 4182417 | 6/1992 |
| WO | 8605390 | 9/1986 |
| WO | 9913837 | 3/1999 |
| WO | 9921530 | 5/1999 |
| WO | 9953889 | 10/1999 |
| WO | 0119946 | 3/2001 |

OTHER PUBLICATIONS

An article entitled Hand Dishwashing Liquid from Solutions Close to Home, Dish Care Formulary HIT–120, Rev. Aug. 1998, BFGoodrich Company, Home Care and I & I.

An article entitled Liquid Water Softener with Zeolite from Solutions Close To Home, Fabric Care Formulary HIT–210, Rev. Aug. 1995, BFGoodrich Company, Home Care and I & I.

An article entitled High Surfactant Gel from Solutions Close To Home, Hard Surface Cleaner Formulary HIT–355, Rev. Apr. 1999, BFGoodrich Company, Home Care and I & I.

An article entitled Carbopol® AQUA 30 Polymer For Home Care and Industrial & Instittional Applications from Solutions Close To Home, PDS Carbopol AQUA 30, Rev. Dec. 1999, BFGoodrich Company, Home Care and I & I.

An article entitled Novel Cosmetic Delivery Systems, edited by Shlomo Magdassi, Elka Touitou, Marcel Dekker, Inc., New York, 1999.

An article entitled Acrysol® ASE–95 Acrylic ThickenerStabilizer, from Rohm and Haas Company, Specialty Chemicals, Rohm and Haas Company, Apr., 1978.

An article entitled Aculyn ™ 22 Thickener For Use in Cosmetic and Toiletry Products by Rohm and Haas Company, Aculyn Personal Care Polymers, Formulation Chemicals, Rohm and Haas Company, 1990.

An article entitled Acusol 820, Detergent Grade Rheology Modifier and Stabilizer from Rohm and Haas Company, Innovative Detergent Polymers, Rohm and Haas, 1995.

An article entitled Acusol 830, Detergent Grade Rheology Modifier and Stabilizer from Rohm and Haas Company, Innovative Detergent Polymers, Rohm and Haas, 1995.

An article entitled Acrysol® Rheology Modifiers and Stabilizers For Personal Care from Rohm and Haas Company, Innovative Personal Care Polymers, Rohm and Haas, 1996.

An article entitled Acrysol® 22 Cosmetic Grade Thickeners from Rohm and Haas Company, Innovative Personal Care Polymers, Rohm and Haas.

An article entitled Acrysol® 33 Cosmetic Grade Rheology Modifier and Stabilizer from Rohm and Haas Company, Innovative Personal Care Polymers, Rohm and Haas.

*Primary Examiner*—Bernard Lipman
(74) *Attorney, Agent, or Firm*—Thoburn T. Dunlap

(57) ABSTRACT

A stable, aqueous composition containing a substantially crosslinked alkali-swellable acrylate copolymer rheology modifier, a surfactant, an alkaline material, and various compounds therein, as for example substantially insoluble materials requiring suspension or stabilization, such as a silicone, an oily material, or a pearlescent material. Additionally, this invention also relates to the formation of a rheologically and phase stable cationic hair dye composition. The invention further relates to the incorporation of an acidic material after the addition of an alkaline material to reduce the pH of the composition without negatively impacting the viscosity of the composition.

13 Claims, 8 Drawing Sheets

Sample   A   B   C   D

Sample         A         C

Sample A
Polymer
"W"

Sample D
Polymer
"Y"

Sample A:
Polymer "W"

Sample B:
No Polymer

Sample C:
Polymer "X"

Sample D:
Polymer "Y"

Sample A:
Polymer "W"

Sample B:
No Polymer

Sample C:
Polymer "X"

Sample D:
Polymer "Y"

Note correction: formula 4A

Sample        A        B        C        D

| Sample | A | B | D |

Sample  A  B  D

Sample      A      C      D

US 6,897,253 B2

STABLE AQUEOUS SURFACTANT COMPOSITIONS

This application claims the benefit of priority from divisional application U.S. Ser. No. 09/547,595 filed on Apr. 11, 2000 now U.S. Pat. No. 6,635,702.

FIELD OF INVENTION

The present invention relates to the formation of stable, aqueous compositions containing a substantially crosslinked alkali-swellable acrylate copolymer rheology modifier, a surfactant, an alkaline material, and various compounds therein, as for example substantially insoluble materials requiring suspension or stabilization, such as a silicone, an oily material, or a pearlescent material. Additionally, this invention also relates to the formation of a rheologically and phase stable cationic hair dye composition. The invention further relates to the incorporation of an acidic material after the addition of an alkaline material to reduce the pH of the composition without negatively impacting the viscosity and rheology of the composition.

BACKGROUND OF THE INVENTION

Heretofore, various substantially insoluble compounds could not be adequately stabilized in an aqueous surfactant containing composition. For example, various aqueous surfactant compositions which contain silicone additives therein, as for example hair or skin conditioners, would separate and/or cream from their surfactant base. Various pearlescent materials, which are often utilized to provide a pearlescent appearance, would have a short shelf life and produce a diminished pearlescent appearance ("flatten out") or actually settle. In other words, instability problems generally existed with regards to the incorporation of silicones and pearlescent materials.

While cationic or basic dyes for hair have been utilized in shampoos to impart temporary color or highlights, the cationic dyes were generally incompatible with the anionic surfactants typically used in traditional shampoo formulas. Accordingly, amphoteric surfactants have been utilized to impart cleansing and detergency properties to the shampoos, but such surfactants do not sufficiently thicken to provide the desired product rheology. While traditional polymeric rheology modifiers, such as carbomers and/or acrylates/$C_{10-30}$ alkyl acrylate cross polymers, have been utilized to increase viscosity, the rheological stability of these compositions is still generally poor.

Various attempts have been made to remedy the above problems.

For example, U.S. Pat. No. 5,656,257 relates to an anionic shampoo and conditioning composition comprising an oily conditioning agent, a shampooing agent, an acrylate copolymer, a cationic conditioning agent, and water. It also relates to the incorporation of a $C_8$–$C_{18}$ fatty acid. The composition utilizes both oily and cationic conditioning agents in combination with an anionic acrylate copolymer for maintaining stability and dispersion.

WO 99/21530 relates to a hair care composition comprising from about 1.00% to about 80.00% by weight of one or more surfactants selected from the group consisting of anionic, nonionic, cationic and zwitterionic surfactants and mixtures thereof; from about 0.05% to about 15.00% by weight of at least one fatty alcohol having from 10 to about 30 carbon atoms; from about 0.10% to about 15.00% by weight of a non-volatile silicone; and from about 1.35% to about 2.70% by weight of a non-crosslinked polymeric suspending agent.

EPO 463,780 relates to a stable, pearly shampoo composition comprising insoluble, non-volatile silicone which may be obtained by including a suspending polymer, to prevent the silicone "creaming" to the top of the bottle in storage, and also to prevent the particles of titanium dioxide coated mica from settling. The composition further relates to an aqueous shampoo composition comprising in addition to water:

(a) from 2 to 40% by weight of a surfactant chosen from anionic, nonionic or amphoteric surfactants, or mixtures thereof;

(b) from 0.01 to 10% by weight of an insoluble, non-volatile silicone;

(c) from 0.1 to 5% by weight of a suspending polymer chosen from polyacrylic acid, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, and heteropolysaccharide gums; and (d) from 0.01 to 5% by weight of titanium dioxide coated mica.

U.S. Pat. No. 4,529,773 relates to compositions containing an associative thickener (a hydrophobically modified alkali-soluble emulsion polymer) that has been activated by neutralization to a pH above 6.5, and subsequently acidified in the presence of a surfactant.

However, the above prior art does not produce sufficiently stabilized aqueous surfactant compositions such as with respect to various silicones, oily materials, pearlescent materials, cationic hair dyes, and other substantially insoluble materials.

SUMMARY OF THE INVENTION

A stable aqueous composition comprises a substantially crosslinked alkali-swellable acrylate copolymer rheology modifier, water, an alkaline material, and an effective amount of a surfactant so that a substantially insoluble compound is stabilized or suspended in the composition. Compositions can be stabilized that contain various volatile and nonvolatile silicone oils, oily materials, and the like. Compositions containing a pearlescent material can be stabilized and which further impart an enhanced pearlescent appearance to the composition. Additionally, compositions containing cationic dyes can be attained and maintained with acceptable rheology. Furthermore, a "Back-Acid" formulation technique can be utilized to achieve low pH compositions. These stable aqueous surfactant compositions can generally maintain a smooth, acceptable rheology, without significant increases or decreases in viscosity or pH, with no separation, settling, or creaming out, over extended periods of time such as for at least one month at 45° C. The polymeric rheology modifier is generally made from one or more carboxylic acid monomers, vinyl monomers, and polyunsaturated monomers. The surfactant can be an anionic, an amphoteric, a zwitterionic, a nonionic, or a cationic surfactant, or combinations thereof.

DETAILED DESCRIPTION OF THE INVENTION

Figure 1:
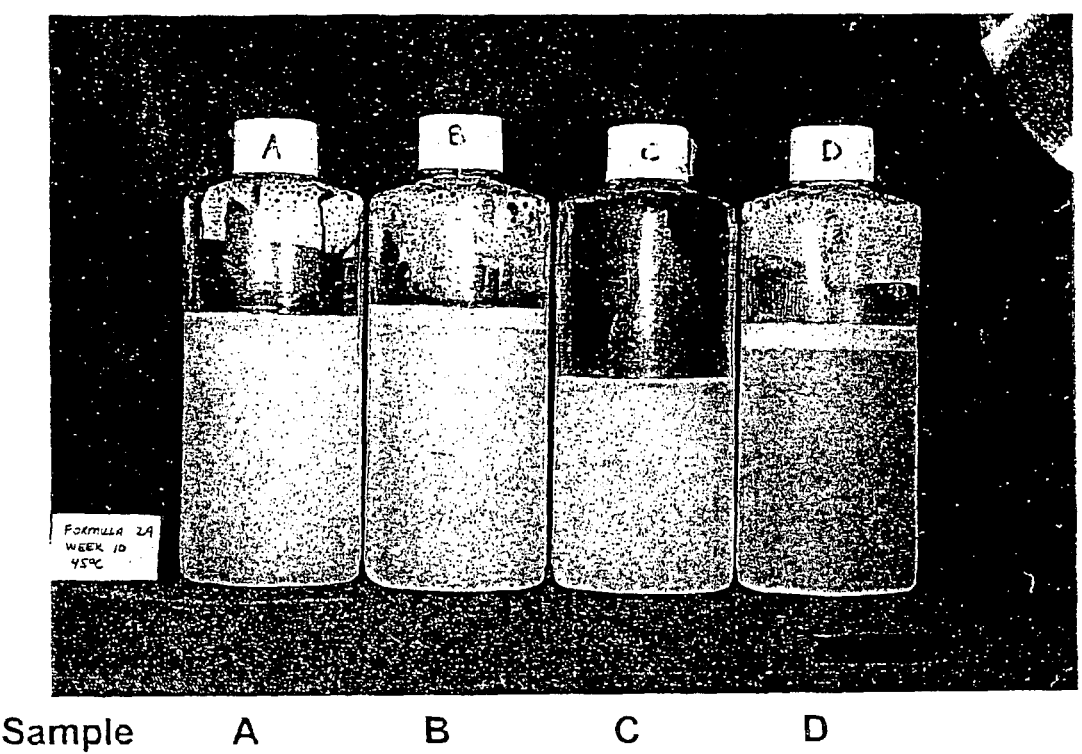
FIG. 1 is a photograph of containers of Example 2A (pearlized 2-in-1 conditioning shampoo) showing stability testing at 45° C. for 10 weeks.

The headings provided herein serve to illustrate, but not to limit the invention in any manner.

Polymeric Rheology Modifier

The polymeric rheology modifier provides various rheological properties, such as flow properties, thickening or viscosity, vertical cling, suspending ability, and Yield Value. Yield Value, also referred to as Yield Stress, is herein defined as the initial resistance to flow under stress. It can be measured using a number of techniques, such as via the use of a constant stress rheometer or via extrapolation using a Brookfield viscometer. These techniques and the usefulness of the Yield Value measurement are further explained in Technical Data Sheet Number 244 available from The B.F.Goodrich Company, herein incorporated by reference. In addition, the polymer is also useful to provide stabilization of insoluble materials, such as particulate matter or oily materials, in the formulation, as well as providing stability to the entire formulation.

The substantially crosslinked alkali-swellable acrylate copolymer rheology modifier of the present invention can generally be prepared by various polymerization routes, such as emulsion, solution, precipitation, and the like, with emulsion polymerization generally being preferred. Emulsion polymerization is generally carried out at a pH of from about 2.5 to about 5.0, with at least three essentially ethylenically unsaturated components. Furthermore, none of these monomers are an associative monomer which is a copolymerizable surfactant capable of nonspecific hydrophobic association similar to those of conventional surfactants.

The polymeric rheology modifier of the present invention generally comprises three structural components. The first component is one or more carboxylic acid monomers having a total of from about 3 to about 10 carbon atoms. Examples of such monomers include but are not limited to acrylic acid, methacrylic acid, itaconic acid, fumaric acid, crotonic acid, maleic acid, or aconitic acid. Moreover, half esters of polyacids, such as maleic acid, fumaric acid, itaconic acid, or aconitic acid and the like with $C_{1-4}$ alkanols can also be used, particularly if it is used in minor amounts in combination with acrylic acid or methacrylic acid.

The amounts of such carboxylic acid monomers is generally from about 20% to 80% by weight, desirably from about 25% to about 70% by weight and preferably from about 35% to about 65% by weight based upon the total weight of the monomers.

The second component is one or more non-acid vinyl monomers which are utilized in an amount of from about 80% to about 15% by weight, desirably from about 75% to about 25% by weight, and preferably from about 65% to about 35% by weight based upon the total weight of the monomers. Such vinyl monomers are ($\alpha,\beta$-ethylenically unsaturated monomers having the formula:

$$CH_2=CXY, \qquad 1)$$

where X is H and Y is —COOR, —$C_6H_4R'$, —CN, —$CONH_2$, —Cl, —$NC_4H_6O$, —$NH(CH_2)_3COOH$, —$NHCOCH_3$, —$CONHC(CH_3)_3$, —CO—$N(CH_3)_2$, or X is $CH_3$ and Y is —COOR, —$C_6H_4R'$, —CN or —CH=$CH_2$;

or X is Cl and Y is Cl, and

R' is $C_1$–$C_{18}$ alkyl, or hydroxy $C_2$–$C_{18}$ alkyl,

R' is H or $C_1$–$C_{18}$ alkyl or having the formula:

$$CH_2=CH\ (OCOR^1); \qquad 2)$$

where $R^1$ is $C_1$–$C_{18}$ alkyl;

or having the formula:

$$CH_2=CH_2 \text{ or } CH_2=CHCH_3. \qquad 3)$$

Typical of such vinyl monomers or mixture of monomers are the various acrylate or hydroxy acrylate esters wherein the ester portion has from 1 to 10 carbon atoms such as methyl acrylate, ethyl acrylate, n-butyl acrylate, 2-ethylhexyl acrylate, 2-hydroxyethyl acrylate, or various vinyl acetates, or styrene, or vinyl chloride, or vinylidene chloride, or acrylonitrile, acrylamide, N,N,-dimethylacrylamide, t-butyl-acrylamide, and their methacrylate analogs.

The third component forming the acrylate rheology modifier is one or more polyunsaturated compounds. Monomeric unsaturated compounds carrying a reactive group that is capable of causing a formed copolymer to be crosslinked before, during, or after polymerization has taken place can also be used.

The various polyunsaturated compounds are utilized to generate either a partially or substantially-crosslinked three-dimensional network. Examples of such polyunsaturated compounds are the polyalkenyl ethers of sucrose, or polyalcohols; diallylphthalates, divinyl benzene, allyl (meth)acrylate, ethylene glycol di(meth)acrylate, methylene bisacrylamide, trimethylolpropane tri(meth)acrylate, diallyl itaconate, diallyl fumarate, diallyl maleate, zinc (meth)acrylate, derivatives of castor oils or polyols made from ethylenically unsaturated carboxylic acid and the like, glycidyl methacrylate, N-methylol acylamide or N-alkoxymethylacrylamide, alkoxy being $C_1$ to $C_{18}$ alcohol; hydroxy(meth)acrylate or (meth)acrylate end-capped caprolactones.

For those skilled in the art of making unsaturated derivatives, a reaction scheme such as an esterification reaction of polyols made from ethylene oxide or propylene oxide or combinations thereof with unsaturated acid such as acrylic acid, methacrylic acid, or with unsaturated anhydride such as maleic anhydride, citraconic anhydride, itaconic anhydride, or an addition reaction with unsaturated isocyanate such as 3-isopropenyl-$\alpha$-$\alpha$-dimethylbenzene isocyanate, is also within the scope of the present invention. Wherever "(meth)." is utilized, it means that the use of the methyl group is optional.

The third component can be used in an amount from about 0.01 to about 5% by weight, desirably from about 0.03 to about 3% by weight, and preferably from about 0.05 to about 1% by weight based upon the total weight of all of the monomers forming said acrylate copolymer rheology modifier.

Furthermore, the crosslinked copolymer rheology modifier is generally free of any moieties derived from associative monomers (i.e. copolymerizable surfactants). Generally free is defined as containing less than about 1% by weight, desirably less than about 0.5% by weight, and preferably less than about 0.2% by weight.

The partially or substantially crosslinked three dimensional network of the present invention can be made in any conventional manner such as set forth in U.S. Pat. No. 4,138,380, or U.S. Pat. No. 4,110,291 which are hereby fully incorporated by reference. Generally, one or more monomers of the above noted carboxylic acid monomers, vinyl monomers, and polyunsaturated monomers are added to a reaction vessel which contains water therein. Suitable amounts of conventional or typical emulsion polymerization surfactants such as sodium lauryl sulfate are added as well as emulsion type initiators, for example sodium or potassium persulfate, redox initiator, and the like. The reaction vessel can also contain a chain transfer agent. The temperature is then increased from about 60° C. to about 100° C. and polymerization commences. Optionally, during the reaction, additional monomers are added over a period of time. Upon completion of the addition of the monomers, polymerization is allowed to run to completion generally by adding additional initiator.

Polymeric rheology modifiers of the present invention are commercially available from The B.F.Goodrich Company under the name of Acrylates Crosspolymer. Preferred are the polymers which provide a viscosity in water of 500 to 10,000 cP (Brookfield RVT, 20 rpm) at 1% active polymer concentration at pH 6–8.

The amount of the one or more substantially crosslinked alkali-swellable acrylate copolymers is generally from about 0.1% to about 10%, desirably from about 0.3% to about 5%, and preferably from about 0.5% to about 3% of active polymer based upon the total weight of the composition.

Surfactant

The stabilized compositions contain various surfactants such as anionic, amphoteric, zwitterionic, nonionic, cationic, or combinations thereof.

The anionic surfactant can be any of the anionic surfactants known or previously used in the art of aqueous surfactant compositions. Suitable anionic surfactants include but are not limited to alkyl sulfates, alkyl ether sulfates, alkaryl sulfonates, alkyl succinates, alkyl sulfosuccinates, N-alkoyl sarcosinates, alkyl phosphates, alkyl ether phosphates, alkyl ether carboxylates, alkylamino acids, alkyl peptides, alkoyl taurates, carboxylic acids, acyl and alkyl glutamates, alkyl isethionates, and alpha-olefin sulfonates, especially their sodium, potassium, magnesium, ammonium and mono-, di- and triethanolamine salts. The alkyl groups generally contain from 8 to 18 carbon atoms and may be unsaturated. The alkyl ether sulfates, alkyl ether phosphates and alkyl ether carboxylates may contain from 1 to 10 ethylene oxide or propylene oxide units per molecule, and preferably contain 1 to 3 ethylene oxide units per molecule.

Examples of suitable anionic surfactants include sodium and ammonium lauryl ether sulfate (with 1, 2, and 3 moles of ethylene oxide), sodium, ammonium, and triethanolamine lauryl sulfate, disodium laureth sulfosuccinate, sodium cocoyl isethionate, sodium C12–14 olefin sulfonate, sodium laureth-6 carboxylate, sodium C12–15 pareth sulfate, sodium methyl cocoyl taurate, sodium dodecylbenzene sulfonate, sodium cocoyl sarcosinate, triethanolamine monolauryl phosphate, and fatty acid soaps.

The nonionic surfactant can be any of the nonionic surfactants known or previously used in the art of aqueous surfactant compositions. Suitable nonioriic surfactants include but are not limited to aliphatic ($C_6$–$C_{18}$) primary or secondary linear or branched chain acids, alcohols or phenols, alkyl ethoxylates, alkyl phenol alkoxylates (especially ethoxylates and mixed ethoxy/propoxy), block alkylene oxide condensate of alkyl phenols, alkylene oxide condensates of alkanols, ethylene oxide/propylene oxide block copolymers, semi-polar nonionics (e.g., amine oxides and phospine oxides), as well as alkyl amine oxides. Other suitable nonionics include mono or di alkyl alkanolamides and alkyl polysaccharides, sorbitan fatty acid esters, polyoxyethylene sorbitan fatty acid esters, polyoxyethylene sorbitol esters, polyoxyethylene acids, and polyoxyethylene alcohols. Examples of suitable nonionic surfactants include coco mono or diethanolamide, coco diglucoside, alkyl polyglucoside, cocamidopropyl and lauramine oxide, polysorbate 20, ethoxylated linear alcohols, cetearyl alcohol, lanolin alcohol, stearic acid, glyceryl stearate, PEG-100 stearate, and oleth 20.

Amphoteric and zwitterionic surfactants are those compounds which have the capacity of behaving either as an acid or a base. These surfactants can be any of the surfactants known or previously used in the art of aqueous surfactant compositions. Suitable materials include but are not limited to alkyl betaines, alkyl amidopropyl betaines, alkyl sulphobetaines, alkyl glycinates, alkyl carboxyglycinates, alkyl amphopropionates, alkyl amidopropyl hydroxysultaines, acyl taurates and acyl glutamates wherein the alkyl and acyl groups have from 8 to 18 carbon atoms. Examples include cocamidopropyl betaine, sodium cocoamphoacetate, cocamidopropyl hydroxysultaine, and sodium cocamphopropionate.

The cationic surfactants can be any of the cationic surfactants known or previously used in the art of aqueous surfactant compositions. Suitable cationic surfactants include but are not limited to alkyl amines, alkyl imidazolines, ethoxylated amines, quaternary compounds, and quaternized esters. In addition, alkyl amine oxides can behave as a cationic surfactant at a low pH. Examples include laoramine oxide, dicetyldimonium chloride, cetrimonium chloride.

Other surfactants which can be utilized in the present invention are set forth in more detail in WO 99/21530, U.S. Pat. Nos. 3,929,678, 4,565,647, 5,720,964, and 5,858,948. Other suitable surfactants are described in *McCutcheon's Emulsifiers and Detergents* (North American and International Editions, by Schwartz, Perry and Berch) which is hereby fully incorporated by reference.

While amounts of surfactant can vary widely, amounts which are often utilized generally range from about 1% to about 80%, desirably from about 5% to about 65%, and preferably from about 6% to about 30% or most preferably from about 8% to 20% weight based upon the total weight of the composition.

Absence of Fatty Acids, Fatty Acid Esters and Fatty Alcohols

The stable, aqueous surfactant containing compositions of the present invention are generally free of "fatty" compounds such as fatty acids, fatty acid esters and fatty alcohols. Fatty acids can generally be classified as mono-carboxylic acids which are derived from the hydrolysis of fats which generally have at least 8 or 10 carbon atoms and often at least 14 carbon atoms or more such as lauric acid, myristic acid, palmitic acid, stearic acid, and the like. Fatty acid esters are made from such fatty acids. The fatty acid alcohols, generally have at least 10 or 12 carbon atoms and more often from about 14 to about 24 carbon atoms that include lauryl alcohol, myristyl alcohol, cetyl alcohol, stearyl alcohol, oleyl alcohol, and the like. By the term "free of" is generally meant that the compositions of the present invention contain generally less than about 5%, 2% or about 1%, desirably less than about 0.5%, 0.2%, or about 0.1%, and preferably less than about 0.05%, 0.03%, or 0.01% by weight or less of fatty acid and/or fatty alcohol.

Insoluble Materials or Compounds

The materials or compounds which require stabilization can be soluble or insoluble in water. Such compounds include insoluble silicones, silicone gums, volatile and non-volatile silicone oils, pearlescent materials, and other types of compounds set forth hereinbelow.

Silicones and Insoluble Oily Compounds

Silicone and oily compounds are often incorporated into a formulation for conditioning, especially on hair and skin, and to improve or impart shine, gloss, water resistance, and or lubricity. These materials can also function as moisture barriers or protectants.

The silicone compound can be insoluble or soluble in water.

Suitable water-insoluble, non-volatile silicone materials include amodimethicone, amodimethicone macroemulsions or microemulsions, polyalkylsiloxanes, poly-arylsiloxanes, polyalkylarylsiloxanes, polysiloxane gums, and polyethersiloxane copolymers. Preferred are high molecular weight polydimethylsiloxanes and emulsions thereof, dimethicones from low to high molecular weight, for example straight chain polydimethysiloxanes (dimethicone) having a viscosity of from about 5 to about 100,000 centistokes (cS), and other silicone materials such as dimethiconol, dimethiconol macroemulsion or microemulsion, phenyidimethicone, polymethylphenyl polysiloxanes, organopolysiloxanes, alkoyxysilicones, polydiorganosiloxanes, polydimethylsiloxane copolymer, and polyaminofunctional silicone, i.e. polyalkylaryl siloxane polyalkylsiloxane, and the like. Water-insoluble silicone materials may also be considered oily conditioning agents. Teachings directed to suitable water-soluble and insoluble silicone materials are found in U.S. Pat. Nos. 4,788,006; 4,341,799; 4,152,416; 3,964,500; 3,208,911; 4,364,837 and 4,465,619, all of which are incorporated herein by reference.

Additional non-soluble, silicone materials which can be utilized include volatile silicones, for example cyclomethicone, or polydimethylsiloxane with a viscosity of 10 cS or less.

Suitable water-soluble silicones include polyether/polysiloxane block copolymers, such as dimethicone copolyol, and derivatives thereof.

Examples of commercially available silicone materials include Dow Corning 200, 345, 3225C, 929 Emulsion, 949 Emulsion, 1664 Emulsion, 1692 Emulsion, 1784 Emulsion, 2-1894 Microemulsion, 184 Emulsion; and General Electric SF-1202, SF18 (350), SF2169, Viscasil 60M, SM2658; and from B.F.Goodrich, such as B.F.Goodrich wax S, C, and F; and others.

Preferred silicone materials used as an oily conditioning agent are polydimethylsiloxanes which have the CTFA designation of dimethicone and which range in viscosity from 5 to 100,000 cS at 25° C., and dimethiconol, and emulsions thereof. A preferred dimethicone has a viscosity of about 60,000 cS and is available from Dow Corning or General Electric.

Other suitable oily materials or conditioning agents include, but are not limited to the following: mineral oils and saturated or unsaturated vegetable oils such as soybean oil, babassu oil, castor oil, cottonseed oil, Chinese tallow oil, crambe oil, perilia oil, Danish rapeseed, rice bran oil, palm oil, palm kernel oil, olive oil, linseed oil, coconut oil, sunflower oil, safflower oil, peanut oil, corn oil, sesame oil, and avocado oil, as well as petrolatum; dlimonene, emollients, Vitamin E, and Vitamin A, and esters such as isopropylpalmitate, cetearyl octanoate, C12–15 alkylbenzoate, octyl stearate, and other materials such as PPG-2 myristyl etherpropionate, and the like.

The silicone or the oily conditioning agent, or combinations thereof comprises between about 0.1% to about 20%, more preferably between about 0.3% to about 7% and most preferably about 0.5% to about 5% by weight of the composition.

Pearlescent Material

Some formulations are often opacified by deliberately incorporating pearlescent materials therein to achieve a cosmetically attractive pearl-like appearance, known as pearlescence. Persons skilled in the art are aware of problems faced by formulators in consistently preparing a pearlescent formulation. A detailed discussion is found in the article "Opacifiers and pearling agents in shampoos" by Hunting, *Cosmetic and Toiletries*, Vol. 96, pages 65–78 (July 1981), incorporated herein by reference.

The pearlescent material includes titanium dioxide coated mica, iron oxide coated mica, ethylene glycol monostearate, ethylene glycol distearate, polyethylene glycol distearate, bismuth oxychloride coated mica, myristyl myristate, guanine, glitter (polyester or metallic), and mixtures thereof. Other pearlescent materials can be found in U.S. Pat. Nos. 4,654,207 and 5,019,376, herein incorporated by reference.

Surprisingly, an improved or enhanced pearlescent appearance has been observed when incorporating said substantially crosslinked alkali-swellable acrylate polymers. A visually perceivable improved appearance is observed initially and especially after the compositions have been aged for 24 hours, as compared to compositions not containing the polymer. Furthermore, the polymer further prevents the sedimentation or precipitation of the pearlescent material thus significantly decreasing the "flattening out" of the pearlescent appearance. Additionally, it is believed that the polymeric rheology modifier serves to hold the pearlescent particles or platelets in their optimal configuration for maximum pearlescent appearance.

The amount of the pearlescent material can generally be used in amounts of from about 0.05% to about 10% and desirably from about 0.15% to about 3% by weight based upon the total weight of the stabilized composition.

Other Insoluble Compounds

In addition to the above generally insoluble compounds, numerous other optional substantially insoluble compounds which require stabilization can be utilized. Examples of such other insoluble compounds include Titanium Dioxide; Pumice; Calcium Carbonate; Talc; Potato Starch; Tapioca Starch; Jojoba Beads; Polyethylene Beads; Walnut Shells; Loofah; Apricot Seeds; Almond Meal; Corn Meal; Paraffin; Oat Bran/Oat Hulls; Gelatin Beads; Alginate Beads; Stainless Steel Fibers; Iron Oxide Pigments; Air Bubbles;. Mica Coated Iron Oxides; Kaolin Clay; Zinc Pyrithione; Salicylic Acid; Zinc Oxide; Zeolite; Styrofoam Beads; Phosphates;

silica, and the like. Other generally insoluble compounds include teatree powder, microsponges, confetti (a trademark of United Guardian Company), talc, beeswax, and the like.

The amount of the various insoluble compounds requiring stabilization will vary depending upon its purpose, desired end result, and efficacy thereof. Hence amounts can vary widely, but frequently will be within a general range of from about 0.1% to about 50% by weight based upon the total weight of the stable composition.

Cationic Dyes for Hair Coloring

The dyes which can be utilized in a temporary hair dye or color maintenance shampoo are generally soluble. Such dyes are generally known to the art and to the literature and are generally referred to as cationic or basic dyes. These dyes are commonly described in two different manners. The dye name (e.g. Basic Brown 16) relates to its INCI name (International Nomenclature Cosmetic Ingredient) and/or its CTFA name (Cosmetic, Toiletry and Fragrance Association) name. Another way to refer to these dyes is through its Color Index number (e.g. CI 12250) which is used by the European Union. Both sets of numbers are set forth in the "International Cosmetic Ingredient Dictionary and Handbook" for example, the 7$^{th}$ Edition, 1997, published by The Cosmetic, Toiletry, and Fragrance Association, Washington, D.C., U.S.A. These cationic dyes are commercially available from Warner Jenkinson under the trademark Arianor. Specific cationic dyes which can be utilized include the various azo dyes such as Basic Brown 16 (CI 12250), Basic Brown 17 (CI 12251), Basic Red 76 (CI 12245), Basic Yellow 57 (CI 12719), as well as various anthraquinone dyes such as Basic Blue 99 (CI 56059) and the like.

The amount of the hair dye when utilized in typical temporary color shampoos is generally from about 0.1 to about 5% by weight based upon the total weight of the stabilized composition.

Alkaline Material

The polymeric rheology modifiers of the present invention are generally supplied in their acidic form. These polymers modify the rheology of a formulation through subsequent neutralization of the carboxyl groups of the polymer. This causes ionic repulsion and a three dimensional expansion of the microgel network thus resulting in an increase in viscosity and other rheological properties. This is also referred to in the literature as a "space filling" mechanism as compared to an associative thickening mechanism.

The alkaline material is therefore incorporated to neutralize the polymer and is preferably a neutralizing agent. Many types of neutralizing agents can be used in the present invention, including inorganic and organic neutralizers. Examples of inorganic bases include but are not limited to the alkali hydroxides (especially sodium, potassium, and ammonium). Examples of organic bases include but are not limited to triethanolamine (TEA), L-arginine, aminomethyl propanol, tromethamine (2-amino 2-hydroxymethyl-1,3-propanediol), PEG-15 cocamine, diisopropanolamine, triisopropanolamine, or tetrahydroxypropyl ethylene diamine. Alternatively, other alkaline materials can be used, such as pre-neutralized surfactants or materials which incorporate a neutralizing agent therein or any other material capable of increasing the pH of the composition.

Acidic Materials

Various acidic materials can be utilized in the present invention such as organic acids, for example citric acid, acetic acid, alpha-hydroxy acid, beta-hydroxy acid, salicylic acid, lactic acid, glycolic acid, or natural fruit acids, or inorganic acids, for example hydrochloric acid, nitric acid, sulfuric acid, sulfamic acid, phosphoric acid, and combinations thereof. Addition of the acidic materials can be at various points in the process, however, the addition of the acidic material after the addition of the alkaline neutralizing agents yields significantly improved rheological properties. This will be discussed in greater detail in the "back acid" formulation technique section.

Other Optional Rheology Modifiers

The composition can optionally contain other rheology modifiers to be used in conjunction with the substantially crosslinked alkali-swellable acrylate copolymer. These polymers are well known in the art and can include natural, semi-synthetic (e.g. clays), or synthetic polymers. Examples of natural or modified natural polymers include but are not limited to gums (e.g., xanthan gum), cellulosics, modified cellulosics, starches, or polysaccharides. Examples of other synthetic polymers include but are not limited to cross-linked polyacrylates, hydrophobically modified alkali-soluble polymers, or hydrophobically modified nonionic urethane polymers. Additionally, the adjustment of viscosity by admixture of salt is also well known and can be employed in the present invention. If present in a composition, these rheology modifiers are generally used from about 0.01 to about 5% by weight of the stable composition.

Biologically Active Materials

The stable aqueous surfactant containing compositions of the present invention can also contain substantially insoluble materials which are biologically active having pharmaceutical, veterinary, biocidal, herbicidal, pesticidal, or other biological activity. Specific examples of such biologically active compounds include acetazolamide; aescin; aesculi hippocastan; allantoine; amfepramone; aminopropylon; amorolfine; androstanolone; arnica; bamethan sulfate; benproperinembonate; benzalkonium chloride; benzocaine; benzoyl peroxide; benzyl nicotinate; betamethasone; betaxolol chlohydrate; buphenine hydrochloride; caffeine; calendula; campher; cetylpyridinium chloride; chloroquin phosphate; clarithromycin; clemastinhydrogene fumarate; clindamycin-2-dihydrogene phosphate; clobetasol-propionate; clotrimazole; codeine phosphate; croconazole; crotamiton; dexamethasone acetate; dexpanthenol; diclofenac; diethylamine salicylate; diflucortolone; diflucortolone valerate; diflucortolone, chlorquinaldol; difluoroprednate; dimethyl sulfoxide; dimeticone 350-silicium dioxide; dimetinden; dimetindenmaleat disopyramide; domperidone; ergotoxine; estradiol; estriol; etofenamate; felbinac; flubendazole; flufenamic acid; fluocinolone; fluocinolone acetonide; fluocortolone; fusidic acid; gelacturoglycani; heparine; hydrocortisone; hydroxyethyl salicylate; ibuprofen; idoxuridine; imidazole salicylate; indomethacin; isoprenaline sulfate; ketoprofen; levomenthol; lidocaine hydrochloride; lindane; menthol; mepyramine; mesalazine; methyl nicotinate; methyl salicylate; metronidazole; miconazole; minoxidil; naftifin; nalixidic acid; naproxen; niflumic acid; nifuratel; nifuratel nystatine; nifuroxazide; nitroglycerin; nonivamid; nystatinnifuratel; omoconazole nitrate; o-rutoside; oxatomide; oxerutin; oxyphenbutazone; pancreatine; pentosane polysulfate; phenolphthalein; phenylbutazone-piperazine; phenylephrine; pilocarpine; piroxicam; plant extracts; polidocanol; polycarbophil; polysaccharide; potassium phosphate; prednisolone; prilocaine; primycin sulphate lidocaine; progesterone; proteins; racem.campher; retacnyl tritinoine; retinol palmitate; salicylamide; salicylic acid; sobrerol; sodium alginate; sodium bicarbonate; sodium fluoride; sodium pentosan polysulfate; sodium phosphate; terpine; theophylline; thromboplastin; thymol; tocopherol acetate; tolmetin; tretinoin; troxerutine; verapamil; viloxazine; vitamine b6; xylitol; xylometazoline; and zincum hyaluronicum; as well as combinations thereof.

Other compounds which can be utilized include the following: 2-ethylhexyl salicylate; adapalene; albendazole; avobenzone; benzalkonium chloride; benzocaine; benzoyl peroxide; betamethasone dipropionate, betaxolo HCl; camphor; capsaicin; clarithromycin; clindamycin phosphate; clobetasol propionate; clocortolone pivalate; crotamiton; desoximetasone; dimethicone; dioxybenzone; erythromycin; ethylhexyl p-methoxycinnamate; fentoin; fluocinonide; guaifenesin; homosalate; hydrocortisone; hydrocortisone valerate; hydroquinone; kaolin; lidocaine; menthol; mesalamine; methyl nicotinate; methyl salicylate; metronidazole; naftifine HCl; nalidixic acid; nitrofurantoin monohydrate; octyl methoxycinnamate; oxybenzone; padimate; pectin; permethrin; phenylbenzimidazole sulfonic acid; phenylpropanolamine HCl; pilocarpine HCl; piperonyl butoxide; prilocaine; progesterone; pyrethrum extract; rimexolone; simethicone; sulfamethoxazole; tretinoin; and zinc chloride; as well as combinations thereof. Still other compounds which can be formulated into control release tablets and used in association with the present invention include: Ascorbic Acid; Aspirin; Atenolol; Caramiphen HCl; Chlorpheniramine Maleate; Dexchlorpheniramine; Diethyl Propion HCl; Diphenhydramine; Ephedrine HCl; Furosemide; Guaifenesin; Isosorbide Dinitrate; Isoanizid; Lithium Carbonate; Mepyramine Meleate; Methadone HCl; Metoclopramide; Nitrofurantoin; Phenylpropanolamine HCl; Pseudoephedrine; Quinidine Gluconate; Quinidine Sulfate; Sodium Valproate; Sulfamethizole; Theophylline; Thiamine; Tridecamine; Verapamil HCl; and Viloxazine; as well as combinations thereof. These compounds are illustrative of those which can be used. Other compounds known to those skilled in the art may also be used.

Other Ingredients

In addition to the above noted compounds, various other ingredients can optionally be utilized in the stable composition of the present invention such as Fragrances, Perfumes, Preservatives, Disinfectants, Antioxidants, Antiredeposition Agents, Carriers, Chelating and Sequestering Agents, Dyes and Pigments, Quaternary Conditioners, Cationic conditioning polymers such as guar hydroxypropyltrimonium chloride, Polyquaternium-4, Polyquaternium-6, Polyquaternium-7, Polyquaternium-10, Polyquaternium-11, Polyquaternium-16, Polyquarternium-24, and Polyquaternium-39, Corrosion Inhibitors, Hydrotropes, Coupling Agents, Defoamers, Builders, Dispersants, Emollients, Extracts, Vitamins, Enzymes, Foam Boosters, Flocculants, Whitening Agents, Fixative Polymers such as PVP, Humectants, Opacifiers, Plasticizers, Powders, Solubilizers, Solvents, Waxes, UV Absorbers/UV Light Stabilizers, Hydrolyzed Proteins, Keratin, Collagens, and the like.

Applications

The stable aqueous surfactant containing compositions of the present invention have a wide number of applications such as personal care applications, home care applications, industrial and institutional applications, pharmaceutical applications, textile compounds, and the like.

Examples of various personal care applications include products such as the following:

Shampoos, for example 2-in-1 Shampoos; Baby Shampoos; Conditioning Shampoos; Bodifying Shampoos; Moisturizing Shampoos; Temporary Hair Color Shampoos; 3-in-1 Shampoos; Anti-Dandruff Shampoos; Hair Color Maintenance Shampoos; Acid (Neutralizing) Shampoos; Salicylic Acid Shampoos;

Skin and Body Cleansers, for example Moisturizing Body Washes; Antibacterial Body Washes; Bath Gels; Shower Gels; Hand Soaps; Bar Soaps; Body Scrubs; Bubble Baths; Facial Scrubs; Foot Scrubs;

Creams and Lotions, for example Alpha-Hydroxy Acid Lotions and Creams; Beta-Hydroxy Acid Creams and Lotions; Skin Whiteners; Self Tanning Lotions; Sunscreen Lotions; Barrier Lotions; Moisturizers; Hair Styling Creams; Vitamin C Creams; Liquid Talc Products and Antibacterial Lotions; and other moisturizing lotions and creams;

Skin and Hair Gels, for example Facial Masks; Body Masks; Hydroalcoholic Gels; Hair Gels; Body Gels; Sunscreen Gels; and the like, as well as other personal care applications such as permanent hair color, and the like.

Examples of home care applications include products such as: home care and industrial and institutional applications, such as laundry detergents; dishwashing detergents (automatic and manual); hard surface cleaners; hand soaps, cleaners and sanitizers; polishes (shoe, furniture, metal, etc.); automotive waxes, polishes, protectants, and cleaners, and the like.

Examples of pharmaceutical applications include topical formulations in the form of creams, lotions, ointments, or gels, where the surfactant may be used as a wetting aid for the pharmaceutically active material, or as a skin penetration enhancer, or as an emulsifier for a solvent phase having an aesthetic effect, or present to enhance the solubility or bioavailability of the pharmaceutically active material. Similar formulations for internal application within the living body, or oral administration, or administration by mechanical means, can be utilized.

These formulations could be administered or applied to either human or veterinary conditions for the full breadth of indications treatable by pharmaceutical means, such as fever, irritation, dermatitis, rash; viral, fungal, or bacterial infection; organic disease; etc.

The pharmaceutically active agents could have any appropriate function for treatment of the condition, and can be a mixture of one or more pharmaceutically active materials, such as emetics, antiemetics, febrifuge, fungicide, biocide, bactericide, antibiotic, antipyretic, NSAID, emollient, analgesics, antineoplastics, cardiovascular agents, CNS stimulants, CNS depressants, enzymes, proteins, hormones, steroids, antipruritics, antirheumatic agents, biologicals, cough and cold treatments, dandruff products, gastrointestinal treatment agents, muscle relaxants, psychotherapeutic agents, skin and mucous membrane agents, skin care products, vaginal preparations, wound care agents, and other appropriate classes of pharmaceutically active agents capable of appropriate administration via dosage form.

Formulating Techniques

The present invention can be made in a number of ways. Generally the one or more substantially crosslinked alkali-swellable acrylate copolymers are added to water and mixed. The surfactant is subsequently added to the aqueous polymeric solution and mixed therein. (Alternatively, the surfactant can be added first to the water followed by the addition of the polymer.) An alkaline material, preferably a neutralizing agent, for example sodium hydroxide, triethanolamine, etc, is then added and mixed to neutralize the solution. The remaining additives including the compound to be stabilized are then added with mixing to produce a desirable end product.

"Back-Acid" Formulating Technique

The polymeric rheology modifiers of the present invention do not start to build substantial viscosity until a pH of about 5 or 6 is achieved. There are some Home and Personal Care applications, however, that require a pH of less than 6 for optimal and desired performance. This has limited the use of such polymers in such compositions. Additionally, it is difficult to even formulate stable applications at this lower pH range.

Surprisingly, it has now been found that if these compositions are raised to a near neutral or even alkaline pH and then subsequently reduced in pH, the viscosity and yield value generally remain unchanged or often actually increase. This formulating technique will be herein referred to as "Back-Acid" thickening. This formulating technique thusly broadens the scope of application of these polymers and now allows for formulation in the acidic pH regime. Additionally, the process of "Back-Acid" thickening can also be used to further increase the viscosity and stability of compositions formulated in the slightly acidic and in the alkaline pH regime.

The one or more acrylate copolymers, polymers, and the like are added to water and mixed. The surfactant is subsequently added to the aqueous polymeric solution and mixed therein. An alkaline material is then added and mixed to increase the pH of the composition to at least about 5, preferably at least about 6, and most preferably at least about 6.5. The alkaline material is preferably a neutralizing agent, such as sodium hydroxide, potassium hydroxide, triethanolamine, or another fatty acid amine neutralizing agent commonly used in said applications. Alternatively, other alkaline materials can be used, such as pre-neutralized surfactants. The pH should desirably be at least about 0.5 or 2 pH units and preferably at least 3, 4, or even 5 pH units above the final target pH of the composition. An acidic material is then added to reduce the pH of the composition.

The material used to decrease the pH of the application is an acidic material, preferably an organic acid, such as citric acid, acetic acid, alpha-hydroxy acid, beta-hydroxy acid, salicylic acid, lactic acid, glycolic acid, natural fruit acids, or combinations thereof. In addition, inorganic acids, for example hydrochloric acid, nitric acid, sulfuric acid, sulfamic acid, phosphoric acid, and combinations thereof can be utilized. The amount of such acid is generally from about 0.1 to about 20%, desirably from about 0.2% to 15%, and preferably from about 0.25% to about 10% by weight based upon the total weight of the stabilized composition.

The desired pH to stabilize compositions of the present invention is obviously dependent on the specific applications. Generally, Personal Care applications have a desired pH range of about 3 to about 7.5, desirably from about 4 to about 6. Generally, Home Care applications have a desired pH range of about 1 to about 12, and desirably from about 3 to about 10. More specifically, when a generally insoluble silicone or pearlescent compound is utilized, a desired pH is from about 5.5 to about 12, whereas when a hair dye is stabilized, the pH is from about 5 to about 9.

Stability:

The various personal care, home care, industrial, institutional, etc. products or compositions made using the substantially crosslinked alkali-swellable acrylate copolymer rheology modifier of the present invention are stable. The stability requirements for a particular composition will vary with its end marketplace application as well as the geography in which it is to be bought and sold. An acceptable "shelf life" is subsequently determined for each composition. This refers to the amount of time that a composition should be stable across its normal storage and handling conditions, measured between the time that the composition is produced and when it is finally sold for consumption. Generally, Personal Care compositions require a 3 year shelf life whereas Home Care compositions require a 1 year shelf life.

To eliminate the need to conduct stability studies in excess of one year, the formulator will conduct stability testing at stressed conditions in order to predict the shelf life of a composition. Typically, accelerated testing is conducted at elevated static temperatures, usually 45–50° C. A composition should be stable for at least 2 weeks, desirably 1 month, preferably 2 or 3 months, and most preferably 4 or 5 months at 45° C. Additionally, freeze-thaw cycling is often employed wherein the composition is cycled between a freezing temperature, usually 0° C., and an ambient temperature, usually 20–25° C. A composition should pass a minimum of 1 freeze-thaw cycle, preferably 3 cycles, and most preferably 5 cycles.

Products or compositions made according to the present invention are considered stable if they meet one or more of the following criteria:

1. There is no phase separation, settling, or creaming of any material in the composition. The composition should remain completely homogenous throughout its bulk. Separation is herein defined as the visible existence of 2 or more distinct layers or phases of any component in the formulation, including but not limited to insoluble matter, soluble matter, oily substances and the like.

2. The viscosity of the composition does not significantly increase or decrease over time, generally less than 50%, preferably less than 35%, and most preferably less than 20%.

3. The pH of the composition does not increase or decrease more than two pH units, preferably not more than one unit, and most preferably not more than one-half unit.

4. The rheology and texture of the composition does not significantly change over time to that which is unacceptable.

Products or compositions made according to the present invention are considered unstable if they do not meet one or more of the above listed criteria.

Further information on stability testing requirements can be found in "The Fundamentals of Stability Testing; IFSCC Monograph Number 2", published on behalf of the International Federation of Societies of Cosmetic Chemists by Micelle Press, Weymouth, Dorset, England, and Cranford, N.J., U.S.A. and is herein incorporated by reference.

Further information on stability of biologically active formulations can be found at: The European Union for the Evaluation of Medicinal Products/Documents Section/ICH Guidelines: http://www.eudra.org/humandocs/humans/ich.htm. (Topic Q1A, Step 2) Note for Guidance on Stability Testing of New Drug Substances and Products (Revision of CPMP/ICH/380/95, released for consultation Nov. 99).

EXAMPLES

The invention will be better understood by reference to the following examples which serve to illustrate but not to limit the scope of the present invention.

In some of the following examples, the formulations were prepared as follows. The noted acrylate copolymer was added to water and mixed. Then, the surfactant was added to the aqueous polymer composition and mixed. Subsequently, the indicated neutralizing agent such as sodium hydroxide was added and mixed. The remaining compounds or ingredients were then added in the order listed with mixing upon the addition of generally each ingredient. Optionally, an acid such as citric acid was subsequently added and mixed.

FORMULATION EXAMPLES

Example 1

Pearlized 3-in-1 Conditioning Shampoo

This formulation demonstrates:
1) A stable, aqueous surfactant composition using the "Back-Acid" formulation technique
2) Stabilization of an insoluble, high molecular weight non-volatile silicone emulsion
3) Suspension and stabilization of a pearlescent material
4) Enhanced pearlescent appearance

| Ingredient | Weight Percent | Function | Trade Name (Supplier) |
|---|---|---|---|
| PART A | | | |
| Deionized Water | qs | Diluent | |
| Acrylates Crosspolymer (30%) | 4.00 | Rheology Modifier | (BFGoodrich) |
| Sodium Laureth Sulfate (2 mole, 25%) | 25.00 | Primary Surfactant | Standapol ES-2 (Henkel) |
| Sodium hydroxide (18%) | 0.75 | Neutralizer | |
| PART B | | | |
| Deionized Water | 5.00 | Diluent | |
| NaOH (18%) | 0.05 | pH Adjuster | |
| Guar Hydroxypropyl Trimonium Chloride | 0.30 | Conditioner | Cosmedia Guar C-261N (Henkel) |
| PART C | | | |
| Lauryl Glucoside (50%) | 4.00 | Co-Surfactant | Plantaren 1200N (Henkel) |
| Sodium Lauryl Sulfate (29%) | 15.00 | Co-Surfactant | Standapol WAQ-Special (Henkel) |
| Glycol Distearate (and) Laureth-4 (and) Cocamidopropylbetaine | 3.00 | Pearlizing Agent | Euperlan PK-3000 (Henkel) |
| Dimethicone (and) Laureth-4 (and) Laureth-23 | 3.00 | Conditioning Agent | DC 1664 Emulsion (Dow Corning) |
| Cocamidopropylbetaine (35%) | 3.00 | Foam Booster | Velvetex BA-35 (Henkel) |
| Coco-Glucoside (and) Glyceryl Oleate | 1.00 | Moisturizer | Lamesoft PO-65 (Henkel) |
| Fragrance | 0.50 | Aesthetic Enhancer | |
| Phenoxyethanol (and) Methylparaben (and) Butylparaben (and) Ethylparaben (and) Propylparaben | 0.50 | Preservative | Phenonip (Nipa) |
| Citric Acid (50%) | 0.40 | pH Adjuster | |
| Properties: | | | |
| Appearance | | Satiny, pearlized viscous liquid | |
| pH | | 5.5–5.8 | |
| Viscosity* (cP) | | 8,000–10,000 | |
| Yield Value** (dynes/cm$^2$) | | 140–160 | |
| Surfactant Actives (%) | | 13.7 | |
| Stability | | Passed 3 months accelerated, 45° C., Passed 5 cycles freeze/thaw | |

*Brookfield DV-II + (or RVT) @ 20, # 5 spindle
**Brookfield DV-II + (or RVT) @1 and 0.5 rp

Examples 2A, 2B and 2C

Pearlized 2-in-1 Conditioning Shampoo

These formulations demonstrate:
1) Stable, aqueous surfactant compositions using the "Back-Acid" formulation technique
2) Stabilization of an insoluble, high molecular weight non-volatile silicone
3) Suspension and stabilization of three different types of pearlescent materials: Guanine, Ethylene glycol distearate, and mica
4) Enhanced pearlescent appearance

| Ingredient | Weight Percent | Function | Trade Name (Supplier) |
|---|---|---|---|
| PART A | | | |
| Deionized Water | qs | Diluent | |
| Acrylates Crosspolymer (30%) | 5.00 | Rheology Modifier | (BFGoodrich) |
| Sodium Laureth Sulfate, (3 mole, 28%) | 30.00 | Primary Surfactant | Standapol ES-3 (Henkel) |
| Sodium hydroxide (18%) | 1.00 | Neutralizer | |
| Cocoamidopropyl Hydroxysultaine (50%) | 10.00 | Co-Surfactant | Mirataine CBS (Rhodia) |
| Disodium Laureth Sulfosuccinate (40%) | 10.00 | Co-Surfactant | Mackanate EL (McIntyre) |
| PART B | | | |
| Deionized Water | qs | Diluent | |
| Pearlizing Agents: | | | |
| Example 2A: Guanine | 0.15 | Aesthetic Enhancer | Mearlmaid AA |
| Example 2B: Glycol distearate sufactant blend | 3.00 | Aesthetic Enhancer | Euperlan PK3000 |
| Example 2C: Mica (and) Titanium Dioxide | 0.20 | Aesthetic Enhancer | Timiron MP115 |
| PART C | | | |
| Dimethicone | 3.00 | Conditioner | Dow Corning 200 Fluid (60,000 cS) |
| Fragrance | 0.50 | Aesthetic Enhancer | |
| Phenoxyethanol (and) Methylparaben (and) Butylparaben (and) Ethylparaben (and) Propylparaben | 0.50 | Preservative | Phenonip (Nipa) |
| Citric Acid (50%) | 0.35 | pH Adjuster | |
| Properties: | | | |
| Appearance | | Viscous, satiny, pearlized liquid | |
| pH | | 5.4–5.7 | |
| Viscosity* (cP) | | 2A = 3,600–6,000 2B = 5,300–8,200 2C = 3,600–6,000 | |
| Yield Value** (dynes/cm$^2$) | | 80–150 | |
| Surfactant Actives (%) | | 17.4 | |
| Stability | | Passed 3 months accelerated, 45° C. Passed 5 cycles freeze/thaw | |

*Brookfield DV-II + (or RVT) @ 20 rpm, 25° C., #4 RV spindle
**Brookfield DV-II + (or RVT) @ 1 and 0.5 rpm

Example 3A and 3B

Clear or Brilliant Gold Pearlized 2-in-1 Conditioning Shampoo

These two formulations are examples of 2-in-1 conditioning shampoos formulating using the "Back-Acid" technique. They also demonstrate the stabilization of an insoluble, non-volatile, high molecular weight amine-functional silicone microemulsion.

Example 3A is a clear formulation at a low pH (about 5).

Example 3B further contains a pearlescent material which is suspended and stabilized. This example also demonstrates the ability of the rheology-modifying polymer to enhance the pearlescent appearance of the formulation.

| Ingredient | Weight Percent | Function | Trade Name (Supplier) |
|---|---|---|---|
| PART A | | | |
| Deionized Water | qs | Diluent | |
| Acrylates Crosspolymer (30%) | 5.00 | Rheology Modifier | (BFGoodrich) |
| Ammonium Lauryl Sulfate (30%) | 40.00 | Primary Surfactant | Stepanol AM (Stepan) |
| Ammonium Laureth Sulfate (3 mole, 27%) | 20.00 | Primary Surfactant | Standapol EA-3 (Henkel) |

-continued

| Ingredient | Weight Percent | Function | Trade Name (Supplier) |
|---|---|---|---|
| NaOH (18%) | 1.40 | Neutralizer | |
| Ammonium Xylene Sulfonate (40%) | 2.50 | Hydrotrope | Stepanate AXS (Stepan) |
| PPG-2 Hydroxyethyl Cocoamide (100%) | 4.00 | Foam Booster | Promidium CO (Mona) |
| Disodium Cocoamphoacetate (50%) | 4.00 | Mild Surfactant | Monateric CLV (Mona) |
| PART B | | | |
| Deionized Water | qs | Diluent | |
| EXAMPLE 3A: Does not contain Mica | | | |
| EXAMPLE 3B: Mica, Titanium Dioxide and Iron Oxides | 0.20 | Aesthetic Enhancer | Cloisonne Sparkle Gold #222J (Englehard) |
| PART C | | | |
| Amodimethicone (and) Trideceth-12 (and) Cetrimonium Chloride | 3.00 | Conditioner | Dow Corning 2–8194 Microemulsion |
| Fragrance | 0.50 | Aesthetic Enhancer | |
| Phenoxyethanol (and) Methylparaben (and) Butylparaben (and) Ethylparaben (and) Propylparaben | 0.50 | Preservative | Phenonip (Nipa) |
| Citric Acid (50%) | 1.70 | pH Adjuster | |
| Properties: | | | |
| Appearance | | 3A = Clear, viscous liquid 3B = Viscous, gold, pearlized liquid | |

| | Before Citric Acid Addition | After Citric Acid Addition |
|---|---|---|
| pH | 6.5 | 5.0 |
| Viscosity* (cP) | 3,300 | 7,800 |
| Yield Value** (dynes/cm$^2$) | 22 | 180 |
| Surfactant Actives (%) | 24.4 | |
| Stability | Passed 3 months accelerated, 45° C. Passed 5 cycles freeze/thaw | |

*Brookfield DV-II + (or RVT) @ 20 rpm, 25° C., #5 RV Spindle
**Brookfield DV-II + (or RVT) @ 1 and 0.5 rpm Example 4A and 4B Salicylic Acid Facial Scrub or Shampoo These two formulations are examples of a salicylic acid facial scrub at a very low pH formulated using the "Back-Acid" technique.

Example 4A demonstrates the suspension and stabilization of an insoluble material, jojoba beads, at a very low pH (about 4)

Example 4B contains a pearlescent material which is suspended and stabilized. This example also demonstrates the ability of the rheology-modifying polymer to enhance the pearlescent appearance of the formulation.

| Ingredient | Weight Percent | Function | Trade Name (Supplier) |
|---|---|---|---|
| PART A | | | |
| Deionized Water | qs | Diluent | |
| Acrylates Crosspolymer (30%) | 5.00 | Rheology Modifier | (BFGoodrich) |
| Alpha Olefin Sulfonate (40%) | 15.00 | Primary Surfactant | Bioterge AS-40 (Stepan) |
| Sodium hydroxide (18%) | 1.00 | Neutralizer | |
| Citric Acid (50%) | 0.50 | pH Adjuster | |
| PART B | | | |
| Deionized Water | 15.00 | Diluent | |
| Alpha Olefin Sulfonate (40%) | 10.00 | Primary Surfactant | Bioterge AS-40 (Stepan) |
| Glycerin | 2.00 | Emollient | |
| Salicylic Acid (USP) | 2.00 | Active | |
| PART C | | | |
| Cocamidopropylbetaine (35%) | 10.00 | Foam Booster | Velvetex BA-35 (Henkel) |

| Ingredient | Weight Percent | Function | Trade Name (Supplier) |
|---|---|---|---|
| FOR EXAMPLE 4A: | | | |
| Potassium $C_{(12-13)}$ Phosphate (40%) | 2.00 | Mild Surfactant | Monafax MAP 230 (Mona) |
| FD&C Red #33 (0.1%) | 0.10 | Aesthetic Enhancer | (BFG Hilton Davis) |
| FD&C Yellow #6 (0.1%) | 0.20 | Aesthetic Enhancer | (BFG Hilton Davis) |
| Jojoba Beads | 2.00 | Aesthetic Enhancer | Florabeads (Floratech) |
| FOR EXAMPLE 4B: | | | |
| Deionized water | qs | Diluent | |
| Mica (and) Titanium Dioxide | 0.20 | Aesthetic Enhancer | Timiron MP 115 (Rona) |
| Properties: | | | |
| Appearance | | 4A = Translucent, viscous liquid with suspended beads  4B = Satiny, white, pearlized viscous liquid | |
| pH | | 3.8–4.0 | |
| Viscosity* (cP) | | 5,500–10,000 | |
| Yield Value** (dynes/cm$^2$) | | 200–350 | |
| Surfactant Actives (%) | | 14.3 | |
| Stability | | Passed 3 months accelerated, 45° C.  Passed 5 cycles freeze/thaw | |

*Brookfield DV-II + (or RVT) @ 20 rpm, 25° C., #4 RV spindle
**Brookfield DV-II + (or RVT) @ 1 and 0.5 rpm Example 5

Pearlized Mild Body Wash

The following formulation is an example of a pearlized mild body wash. This formulation demonstrates the following:

1) A stable, aqueous surfactant composition using the "Back-Acid" formulation technique
2) Stabilization of an insoluble, high molecular weight non-volatile silicone gum emulsion
3) Suspension and stabilization of a pearlescent material
4) Enhanced pearlescent appearance

| Ingredient | Weight Percent | Function | Trade Name (Supplier) |
|---|---|---|---|
| PART A | | | |
| Deionized Water | 14.45 | Diluent | |
| Acrylates Crosspolymer (30%) | 5.00 | Rheology Modifier | (BFGoodrich) |
| Cocoyl Isethionate (and) Sodium Lauroamphoacetate (and) Sodium Methyl Cocoyl Taurate (and) Sodium Xylene Sulfonate (38%) | 45.00 | Primary Surfactant Blend | Miracare UM-140 (Rhodia) |
| Sodium Laureth Sulfate (2 mole, 27%) | 15.00 | Primary Surfactant | Rhodapex ES-2 (Rhodia) |
| PART B | | | |
| Deionized Water | 5.00 | Diluent | |
| NaOH (18%) | 0.05 | pH Adjuster | |
| Guar Hydroxypropyl Trimonium Chloride | 0.15 | Conditioning Agent | Jaguar C-14S (Rhodia) |
| Citric Acid (50%) | 0.05 | pH Adjuster | |
| PART C | | | |
| Sodium Cocoamphoacetate (37%) | 5.00 | Co-Surfactant | Miranol Ultra C37 (Rhodia) |
| Polyquaternium-7 | 2.00 | Conditioner | Mirapol 550 (Rhodia) |
| Dimethiconol (and) TEA-Dodecylbenzenesulfonate | 4.00 | Conditioner | DC 1784 Emulsion (Dow Corning) |
| PART D | | | |
| Deionized Water | 2.50 | Diluent | |
| Mica (and) Titanium Dioxide | 0.20 | Aesthetic Enhancer | Flamenco Satin Pearl 3500 (Englehard) |
| PART E | | | |
| Fragrance | 0.50 | Aesthetic Enhancer | |
| Phenoxyethanol (and) Methylparaben (and) Butylparaben (and) | 0.50 | Preservative | Phenonip (Nipa) |

-continued

| Ingredient | Weight Percent | Function | Trade Name (Supplier) |
|---|---|---|---|
| Ethylparaben (and) Propylparaben | | | |
| Citric Acid (50%) | 0.60 | pH Adjuster | |
| Properties: | | | |
| Appearance | | Viscous, satiny, pearlized liquid | |
| pH | | 6.4–6.8 | |
| Viscosity* (cP) | | 17,000–22,000 | |
| Yield Value** (dynes/cm$^2$) | | 100–150 | |
| Surfactant Actives (%) | | 23.0 | |
| Stability | | Passed 3 months accelerated, 45° C. Passed 5 cycles freeze/thaw | |

*Brookfield DV-II + (or RVT) @ 20 rpm, 25° C., #6 RV spindle
**Brookfield DV-II + (or RVT) @ 1 and 0.5 rpm

Example 6

Clear Bath Gel with Suspended Beads

The following formulation is an example of a clear bath gel with suspended beads. This formulation demonstrates the following:
1) A stable, aqueous surfactant composition
2) Suspension and stabilization of an insoluble material, gelatin beads with mineral oil

| Ingredient | Weight Percent | Function | Trade Name (Supplier) |
|---|---|---|---|
| Deionized Water | qs | Diluent | |
| Acrylates Crosspolymer (30%) | 8.00 | Rheology Modifier | (BFGoodrich) |
| Sodium Laureth Sulfate (2 mole, 28%) | 37.30 | Primary Surfactant | Texapon NSO (Henkel) |
| Sodium hydroxide (18%) | 1.32 | Neutralizer | |
| Cocamidopropylbetaine (30%) | 2.10 | Foam Booster | Tegobetaine L (Goldschmidtl) |
| Polyquaternium-39 | 2.10 | Conditioning Agent | Merquat 3330 (Calgon) |
| Tetrasodium EDTA | 0.05 | Chelating Agent | |
| Fragrance | 0.50 | Fragrance | |
| Polysorbate 20 | 0.50 | Solubilizer | Tween-20 |
| White Beads with Vitamin E | 1.00 | Moisturizer | Lipopearls (Lipo Technologies) |
| Properties: | | | |
| Appearance | | Viscous, clear liquid | |
| pH | | 6.3–6.7 | |
| Viscosity* (cP) | | 4,000–6,000 cP | |
| Yield Value** (dynes/cm$^2$) | | 120–220 | |
| Surfactant Actives (%) | | 11.1 | |
| Stability | | Passed 3 months accelerated 45° C. Passed 5 cycles freeze/thaw | |

*Brookfield DV-II + (or RVT) @ 20 rpm, 25° C., #4 RV spindle
**Brookfield DV-II + (or RVT) @ 1 and 0.5 rpm

Example 7

Temporary Color Shampoo (Medium Brown)

The following formulation is an example of a temporary color shampoo or color maintenance shampoo. This formulation demonstrates the following:

1) A stable viscous temporary hair color composition using cationic dyes
2) Suspension and stabilization of a pearlescent material
3) Enhanced pearlescent appearance
4) Improved rheological properties

| Ingredient | Weight Percent | Function | Trade Name (Supplier) |
|---|---|---|---|
| PART A | | | |
| Deionized water | 41.85 | Diluent | |
| Acrylates Crosspolymer (30%) | 10.00 | Rheology modifier | (BFGoodrich) |
| PART B | | | |
| Deionized water (heated to 50° C.) | 15.00 | Diluent | |
| Disodium EDTA | 0.05 | Chelator | |
| Butylene Glycol | 5.00 | Solvent | |
| Sodium cocoamphoacetate (37%) | 15.00 | Surfactant | Miranol Ultra C-37 (Rhodia) |
| Cocamidopropyl betaine (35%) | 3.00 | Surfactant | Proteric CAB (Protameen) |
| Polyquaternium-39 | 0.80 | Hair conditioner | Merquat Plus 3330 (Calgon) |
| Propylene Glycol (and) Diazolidinyl Urea (and) Methylparaben (and) Propylparaben | 0.45 | Preservative | Germaben II (ISP) |
| Sodium Hydroxide (18%) | 0.25 | Neutralizer | |
| PART C | | | |
| Deionized water (heated to 50° C.) | 10.00 | Diluent | |
| Basic Brown 17/Cl 12251 | 0.25 | Dye | Arianor Sienna Brown (Tri-K/Warner Jenkinson) |
| Basic Blue 99/Cl 56059 | 0.125 | Dye | Arianor Steel Blue (Tri-K/Warner Jenkinson) |
| Basic Red 76/Cl 12245 | 0.125 | Dye | Arianor Madder Red (Tri-K/Warner Jenkinson) |
| Dimethicone copolyol | 0.20 | Hair conditioner | DC 193 Surfactant (Dow Corning) |
| PART D | | | |
| Decyl glucoside (50%) | 4.00 | Surfactant | Plantaren 2000 (Henkel Cospha) |
| Deionized water | 3.00 | Diluent | |
| Mica (and) Titanium dioxide | 0.20 | Pearlizing agent | Timiron MP-149 Diamond Cluster (Rona) |
| Properties: | | | |
| Appearance | | Dark brown, pearlescent viscous liquid | |
| pH | | 6.8–7.4 | |
| Viscosity* (cP) | | 5,000–7,000 | |
| Yield Value** (dynes/cm$^2$) | | 300–400 | |
| Surfactant Actives (%) | | 8.6 | |
| Stability | | Passed 3 months accelerated, 45° C. Passed 7 cycles freeze/thaw | |

*Brookfield DV-II + (or RVT) @ 20 rpm, #4 spindle
**Brookfield DV-II + (or RVT) @ 1 and 0.5 rpm Example 8

Anti-dandruff Shampoo

The following formulation is an example of a conditioning anti-dandruff shampoo. This formulation demonstrates the following:
1) A stable, aqueous surfactant composition using the "Back-Acid" formulation technique
2) Stabilization of an insoluble, high molecular weight non-volatile silicone gum emulsion
3) Suspension and stabilization of an insoluble anti-dandruff material; zinc pyrithione

| Ingredient | Weight Percent | Function | Trade Name (Supplier) |
|---|---|---|---|
| PART A | | | |
| Deionized Water | qs | Diluent | |
| Acrylates Crosspolymer (30%) | 5.00 | Rheology Modifier | (BFGoodrich) |
| Sodium Lauryl Sulfate (29%) | 16.00 | Primary Surfactant | Standapol WAQ-LC (Henkel) |
| Sodium Laureth Sulfate (2 mole, 25%) | 16.00 | Primary Surfactant | Standapol ES-2 (Henkel) |
| Sodium hydroxide (18%) | 0.65 | Neutralizer | |
| PART B | | | |
| Deionized Water | 10.00 | Diluent | |
| Polyquaternium-10 | 0.25 | Hair Conditioner | Ucare Polymer JR-400 (Amerchol) |
| DMDM Hydantoin | 0.30 | Preservative | Glydant (Lonza) |
| PART C | | | |
| Cocamidopropylbetaine (35%) | 4.00 | Foam Enhancer | Velvetex BA-35 (Henkel) |
| Citric Acid (50%) | 0.75 | pH Adjuster | |
| Zinc Pyrithione (48%) | 2.50 | Active | Zinc Omadine (Arch Chemical) |
| Dimethiconol (and) TEA-Dodecylbenzenesulfonate | 3.00 | Conditioner | DC 1784 Emulsion (Dow Corning) |
| FD&C Blue #1 (0.1%) | 1.00 | Dye | (BFG Hilton Davis) |
| Fragrance | 0.50 | Fragrance | |
| Sodium Chloride | 0.60 | Viscosity Enhancer | |
| Properties: | | | |
| Appearance | | Blue, opaque, viscous liquid | |
| pH | | 5.4–5.7 | |
| Viscosity* (cP) | | 3,500–5,000 | |
| Yield Value** (dynes/cm$^2$) | | 120–170 | |
| Surfactant Actives | | 11.5 | |
| Stability | | Passed 1 month accelerated, 45° C. | |

*Brookfield DV-II + (or RVT) @ 20 rpm, 25° C., #4 spindle
**Brookfield DV-II + (or RVT) @ 1 and 0.5 rpm

Example 9

Clear Bath Gel with Suspended Beads

The following formulation is an example of a clear bath gel with suspended beads. This formulation demonstrates the following:

1) A stable, aqueous surfactant composition
2) Suspension and stabilization of an insoluble material, gelatin beads with mineral oil

| Ingredient | Weight Percent | Function | Trade Name (Supplier) |
|---|---|---|---|
| PART A | | | |
| Deionized Water | 42.03 | Diluent | |
| Acrylates Crosspolymer (30%) | 10.00 | Rheology Modifier | (BFGoodrich) |
| Sodium Laureth Sulfate (3 mole, 28%) | 30.00 | Primary Surfactant | Standapol ES-3 (Henkel) |
| Sodium hydroxide (18%) | 1.90 | Neutralizer | |
| Propylene Glycol | 2.00 | Humectant | |
| PART B | | | |
| Deionized Water | 5.00 | Diluent | |
| Benzophenone-4 | 0.02 | UV Absorber | Uvinul MS-40 (BASF) |
| Disodium EDTA | 0.10 | Chelating Agent | |

-continued

| Ingredient | Weight Percent | Function | Trade Name (Supplier) |
|---|---|---|---|
| PART C | | | |
| Cocoamidopropylbetaine (35%) | 4.00 | Foam Enhancer | Incronam 30 (Croda) |
| PART D | | | |
| Polysorbate 20 | 0.80 | Solubilizer | Tween 20 (ICI) |
| Fragrance | 0.60 | Fragrance | |
| Propylene Glycol, Diazolidinyl Urea, Methylparaben, Propylparaben | 1.00 | Preservative | Germaben II (Sutton) |
| White Beads w/Vitamin E | 1.00 | Moisturizer | Lipopearls (Lipo Technologies) |
| FD&C Blue #1 (0.1%) | 0.05 | Dye | (BFG Hilton Davis) |
| FD&C Green #5 (0.1%) | 1.50 | Dye | (BFG Hilton Davis) |
| Properties: | | | |
| Appearance | | Viscous, clear liquid | |

| | Before Citric Acid Addition | After Citric Acid Addition |
|---|---|---|
| pH | 6.5 | 4.5 |
| Viscosity* (cP) | 4,600 | 5,500 |
| Yield Value** (dynes/cm$^2$) | 270 | 440 |
| Surfactant Actives (%) | 10.6 | |
| Stability | Passed 3 months accelerated, 45° C. Passed 5 cycles freeze/thaw | |

*Brookfield DV-II + (or RVT) @ 20 rpm, 25° C., #4 RV spindle
**Brookfield DV-II + (or RVT) @ 1 and 0.5 rpm Example 10

Alpha Hydroxy Acid Cream

The following formulation is an example of an AHA (alpha-hydroxy acid) lotion. This formulation demonstrates the following:
1) A stable, aqueous surfactant-based emulsion composition using the "Back-Acid" formulation technique.
2) Rheology modification and stabilization of an emulsion containing a high level of an alpha hydroxy acid (about 6%) at a very low pH (about 4)
3) Stabilization of insoluble, non-volatile silicone (dimethicone) and other oily materials (isopropyl palmitate and mineral oil) in an emulsion

| Ingredient | Weight Percent | Function | Trade Name (Supplier) |
|---|---|---|---|
| PART A | | | |
| Deionized Water | 51.55 | Diluent | |
| Glycerin | 4.80 | Humectant | |
| Triethanolamine (99%) | 0.75 | Neutralizing Agent | |
| PART B | | | |
| Cetyl Alcohol | 2.85 | Opacifier | |
| Glyceryl Stearate (and) PEG-100 Stearate | 4.25 | Emulsifier | Arlacel 165 (ICI Surfactants) |
| Stearic Acid (3X) | 1.45 | Emulsifier | |
| Isopropyl Palmitate | 4.25 | Emollient | |
| Mineral Oil (and) Lanolin Alcohol | 4.25 | Emollient | Amerchol 101 (Amerchol) |
| Dimethicone | 1.45 | Emollient | DC 200 Fluid (350 cS) (Dow Corning) |
| PART C | | | |
| Acrylates Crosspolymer (30%) | 5.00 | Rheology Modifier | (BFGoodrich) |
| Lactic Acid (45% Soln.) | 13.40 | Active | |

-continued

| Ingredient | Weight Percent | Function | Trade Name (Supplier) |
|---|---|---|---|
| Triethanolamine | 5.00 | Neutralizer | |
| Propylene Glycol (and) Diazolidinyl Urea (and) Methylparaben (and) Propylparaben | 1.00 | Preservative | Germaben II (Sutton) |
| Properties: | | | |
| Appearance | | Thick, white cream | |
| pH | | 3.8–4.1 | |
| Viscosity* (cP) | | 16,000–18,000 | |
| Surfactant Actives (%) | | 5.7 | |
| Stability | | Passed 1 month accelerated, 45° C. Passed 3 cycles freeze/thaw | |

*Brookfield DV-II + (or RVT) @ 20 rpm, 25° C., #6 RV spindle

Preparation Procedure

1. Part A: Add glycerin and triethanolamine to deionized water. Heat to 65° C.
2. Part B: Combine all in separate vessel and heat until melted. Add to Part A with vigorous agitation. Allow to cool to ~40° C. with mixing.
3. Slowly add in the Acrylates Crosspolymer while mixing.
4. Slowly add lactic acid solution while mixing.
5. Adjust pH to 4.0 with triethanolamine.
6. Add the preservative.

Example 11

Facial Cream

The following formulation is an example of a facial cream. This formulation demonstrates the following:
1) An aqueous surfactant-based emulsion composition
2) Stabilization of insoluble, volatile silicone (cyclomethicone), non-volatile silicone (dimethicone) and other oily materials (sunflower oil, cetearyl octanoate and PPG-2 myristyl ether propionate) in an emulsion

| Ingredient | Weight Percent | Function | Trade Name (Supplier) |
|---|---|---|---|
| PART A (heated to 55° C.) | | | |
| Deionized Water | 76.80 | Diluent | |
| Glycerin | 2.50 | Humectant | |
| PART B (heated to 55° C.) | | | |
| PPG-2 Myristyl Ether Propionate | 2.00 | Emollient | Crodamol PMP (Croda) |
| Cetearyl Octanoate | 3.25 | Emollient | Crodamol CAP (Croda) |
| Sunflower Oil | 3.00 | Emollient | |
| Cetyl Alcohol | 1.50 | Emulsifier | Lanette 16 NF (Henkel) |
| Cetearyl Alcohol/Ceteareth-20 | 3.00 | Emulsifier | Emulgade 1000 NI (Henkel) |
| PART C | | | |
| Acrylates Crosspolymer (30%) | 5.00 | Rheology Modifier | (BFGoodrich) |
| Sodium hydroxide (18%) (to pH 6.5) | 0.95 | Neutralizer | |
| PART D (added at 40° C.) | | | |
| Cyclomethicone (and) Dimethicone | 1.00 | Lubricant | DC 1401 Fluid (Dow Corning) |

-continued

| Ingredient | Weight Percent | Function | Trade Name (Supplier) |
|---|---|---|---|
| PART E | | | |
| Propylene Glycol (and) Diazolidinyl Urea (and) Methylparaben (and) Propylparaben | 1.00 | Preservative | Germaben II-E (Sutton) |
| Properties: | | | |
| Appearance | | White, viscous emulsion | |
| pH | | 6.0–7.0 | |
| Viscosity* (cP) | | 10,000–20,000 | |
| Surfactant Actives (%) | | 4.5 | |

*Brookfield DV-II + (or RVT) @ 20 rpm, 25° C., #6 spindle

Example 12

Body Lotion

The following formulation is an example of a body lotion. This formulation demonstrates the following:
1) An aqueous surfactant-based emulsion
2) Stabilization of insoluble, volatile silicone (cyclomethicone), non-volatile silicone (dimethicone) and other oily materials (C12–15 alkyl benzoate, octyl stearate, and mineral oil.)

| Ingredient | Weight Percent | Function | Trade Name (Supplier) |
|---|---|---|---|
| Part A | | | |
| Deionized Water | 76.80 | Diluent | |
| Glycerin | 2.50 | Humectant | |
| Part B | | | |
| Mineral Oil | 4.00 | Emollient | Drakeol 21 (Penreco) |
| C12-15 Alkyl Benzoate | 2.50 | Emollient | Finsolv TN (Finetex) |
| Octyl Stearate | 1.75 | Emollient | Cetiol 868 (Henkel) |
| Cetyl Alcohol | 1.50 | Emulsifier | Lanette 16 NF (Henkel) |
| Cetearyl Alcohol/Ceteareth-20 | 3.00 | Emulsifier | Emulgade 1000 NI (Henkel) |

-continued

| Ingredient | Weight Percent | Function | Trade Name (Supplier) |
|---|---|---|---|
| Part C | | | |
| Acrylates Crosspolymer (30%) | 5.00 | Rheology Modifier | (BFGoodrich) |
| Sodium hydroxide (18%) | 0.95 | Neutralizer | |
| Part D | | | |
| Cyclomethicone (and) Dimethicone | 1.00 | Lubricant | DC 1401 Fluid (Dow Corning) |
| Part E | | | |
| Propylene Glycol (and) Diazolidinyl Urea (and) Methylparaben (and) Propylparaben | 1.00 | Preservative | Germaben II-E (Sutton) |
| Properties: | | | |
| Appearance | | White lotion | |
| pH | | 6.0–7.0 | |
| Viscosity* (cP) | | 15,000–25,000 | |
| Surfactant Actives (%) | | 4.5 | |

*Brookfield DV-II + (or RVT) @ 20 rpm, 25° C., #6 spindle

Example 13 d-Limonene Cleanser

The following formulation is an example of a d-Limonene cleanser. This formulation demonstrates the following:

1) An aqueous surfactant-based emulsion composition using the "Back-Acid" formulation technique
2) Stabilization and co-emulsification of an insoluble oily material (d-Limonene) in an emulsion with a very low level of surfactant

| Ingredient | Weight Percent | Function | Trade Name (Supplier) |
|---|---|---|---|
| Deionized Water | q.s. | Diluent | |
| Acrylates Crosspolymer (30%) | 4.00 | Stabilizer | (BFGoodrich) |
| d-Limonene | 25.00 | Solvent | Arylessence |
| Propylene Glycol | 1.00 | Humectant | |
| Glycerin | 2.00 | Humectant | |
| $C_{12-15}$ Pareth-7 | 1.00 | Surfactant | Neodol 25-7 (Shell) |
| Propylene Glycol (and) Diazolidinyl Urea (and) Methylparaben (and) Propylparaben | 1.00 | Preservative | Germaben II-E (Sutton Labs) |
| Sodium hydroxide (18%) | 1.20 | Neutralizing Agent | |
| Citric Acid (50%) | 0.25 | pH adjusted | |
| Properties: | | | |
| Appearance | | opaque, white, low viscosity, sprayable lotion | |

| | Before Citric Acid Addition | After Citric Acid Addition |
|---|---|---|
| pH | 7.8 | 6.8 |
| Viscosity* (cP) | 6,500 | 11,300 |
| Yield Value** (dynes/cm2) | 520 | 1,380 |
| Surfactant Actives (%) | 1.0 | |

*Brookfield DV-II + (or RVT) @ 20 rpm, 25° C., #3 spindle
**Brookfield DV-II + (or RVT) @ 1 and 0.5 rpm Example 14

Liquid Detergent

The following formulation is an example of a composition useful for a wide variety of cleansing applications, such as for manual dishwashing. This formulation demonstrates the use of the "Back-Acid" formulation technique to substantially increase the viscosity. Furthermore, the substantial increase in yield value as a result of the "Back-Acid" formulation technique would allow for the suspension of insoluble compounds.

| Ingredient | Weight Percent | Function | Trade Name (Supplier) |
|---|---|---|---|
| Deionized Water | Q.S. | Diluent | |
| Acrylates Crosspolymer (30%) | 5.50 | Rheology Modifier | (BFGoodrich) |
| Ammonium lauryl sulfate (28%) | 25.00 | Surfactant | Standapol A (Henkel) |
| Sodium Lauryl ether sulfate (2 mole, 25%) | 25.00 | Surfactant | Standapol ES-2 (Henkel) |
| Sodium hydroxide (18%) | 1.00 | pH Adjuster | |
| Citric acid (50%) | q.s. | pH Adjuster | |
| Properties: | | | |
| Appearance | | Viscous liquid | |

| | Before Citric Acid Addition | After Citric Acid Addition |
|---|---|---|
| pH | 7.0 | 5.0 |
| Viscosity* (cP) | 1,825 | 4,550 |
| Yield Value** (dynes/cm$^2$) | 25 | 170 |
| Surfactant Actives (%) | 13.3 | |

*Brookfield DV-II + (or RVT) @ 20, # 5 spindle
**Brookfield DV-II + (or RVT) @ 1 and 0.5 rpm Example 15

Heavy-Duty Liquid Detergent

The following formulation is an example of a composition useful for a wide variety of cleansing applications, such as for manual dishwashing or fabric washing. This formulation demonstrates the use of the "Back-Acid" formulation technique to substantially increase the viscosity. Furthermore, the substantial increase in yield value as a result of the "Back-Acid" formulation technique would allow for the suspension of insoluble compounds.

| Ingredient | Weight Percent | Function | Trade Name (Supplier) |
|---|---|---|---|
| Deionized Water | Q.S. | Diluent | |
| Acrylates Crosspolymer (30%) | 5.00 | Rheology Modifier | (BFGoodrich) |
| Sodium lauryl ether sulfate, 3 mole EO (28%) | 75.00 | Surfactant | Standapol ES-3 (Henkel) |
| $C_{12-13}$ ethoxylated linear alcohol, 1 mole EO | 2.00 | Surfactant | Neodol 23-1 (Shell) |
| Sodium hydroxide (18%) | 1.00 | pH Adjuster | |
| Citric acid (50%) | 4.00 | pH Adjuster | |
| Properties: | | | |
| Appearance | | viscous liquid | |
| pH | | 3.0–4.0 | |
| Viscosity* (cP) | | 9,000–10,000 | |
| Surfactant Actives (%) | | 21.0 | |

*Brookfield DV-II + (or RVT) @ 20, # 5 spindle

Example 16

Heavy-Duty Liquid Detergent

The following formulation is an example of a composition useful for a wide variety of cleansing applications, such as for manual dishwashing or fabric washing. This formulation combines the substantially cross-linked alkali-swellable acrylate rheology modifier with a standard cross-linked polyacrylate polymer. This formula further demonstrates the use of the "Back-Acid" formulation technique to substantially increase the viscosity. Furthermore, the substantial increase in yield value as a result of the "Back-Acid" formulation technique would allow for the suspension of insoluble compounds.

| Ingredient | Weight Percent | Function | Trade Name (Supplier) |
|---|---|---|---|
| Deionized Water | Q.S. | Diluent | |
| Acrylates Crosspolymer (30%) | 5.00 | Rheology Modifier | (BFGoodrich) |
| Carbomer | 0.75 | Rheology Modifier | Carbopol EZ-1 (BFGoodrich) |
| Sodium Lauryl ether sulfate, 2 moles EO (25%) | 70.00 | Surfactant | Standapol ES-2 (Henkel) |
| Sodium hydroxide (18%) | 1.00 | pH Adjuster | |
| Citric acid (50%) | 4.00 | pH Adjuster | |
| Properties: | | | |
| Appearance | viscous liquid | | |
| pH | 4.0 | | |
| Viscosity* (cP) | 42,000 | | |
| Surfactant Actives (%) | 17.5 | | |

*Brookfield DV-II + (or RVT) @ 20, # 5 spindle

Example 17

Heavy-Duty Liquid Detergent

The following formulation is an example of a composition useful for a wide variety of cleansing applications, such as for fabric washing. This formulation demonstrates the use of the "Back-Acid" formulation technique to substantially increase the viscosity. This example, however, demonstrates the capability to increase the pH of the composition to a very alkaline pH followed by a reduction to a near neutral pH. Furthermore, the substantial increase in yield value as a result of the "Back-Acid" formulation technique would allow for the suspension of insoluble compounds.

| Ingredient | Weight Percent | Function | Trade Name (Supplier) |
|---|---|---|---|
| Water | Q.S. | Diluent | |
| Acrylates Crosspolymer (30%) | 7.00 | Rheology Modifier | (BFGoodrich) |
| Alkylbenzene Sulfonic Acid (97%) | 13.50 | Surfactant | Biosoft S-100 (Stepan) |
| Sodium lauryl sulfate (29%) | 7.50 | Surfactant | Standapol WAQ (Henkel) |
| Sodium lauryl ether sulfate, 2 moles EO (25%) | 7.50 | Surfactant | Standapol ES-2 (Henkel) |
| Alkyl polyglucoside (50%) | 5.00 | Surfactant | Glucopon 600 CS (Henkel) |
| Coconut fatty acid | 3.50 | Surfactant | |
| Triethanolamine (99%) | 7.00 | pH Adjuster | |
| Glycerin | 2.00 | Solvent | |
| NaOH (50%) | 8.60 | pH Adjuster | |
| Citric acid (50%) | 8.00 | pH Adjuster | |
| Properties: | | | |
| Appearance | Viscous gel | | |
| pH before citric acid addition | 13.0 | | |
| pH after citric acid addition | 8.0 | | |
| Viscosity* (cP) | 15,000 | | |
| Yield Value** (dynes/cm$^2$) | 180 | | |
| Surfactant Actives | 23.2 | | |

*Brookfield DV-II + (or RVT) @ 20, # 5 spindle
**Brookfield DV-II + (or RVT) @ 1 and 0.5 rpm

Comparative Stability Testing

Select example formulations were formulated with different polymeric rheology modifiers:

| Sample | Polymer Code | Description |
|---|---|---|
| A | "W" | Acrylates Crosspolymer (present invention) |
| B | | No Polymer |
| C | "X" | Acrylates/Ceteth-20 Methacrylate Copolymer |
| D | "Y" | Acrylates/C10–30 Alkyl Acrylate Crosspolymer |

The viscosity of experiments made with "No Polymer" were adjusted to the desired viscosity range of each formula using sodium chloride. Equal amounts by weight of "Polymer W" and "Polymer X" were used in each formula. The amount of "Polymer Y" was determined by the desired formulation viscosity.

TABLE 1

| Example # | Sample A | | | Sample B | | | Sample C | | | Sample D | | |
|---|---|---|---|---|---|---|---|---|---|---|---|---|
| | STAB | SEP | DAY | STAB | SEP | DAY | STAB | SEP | DAY | STAB | SEP | DAY |
| 1 | S | 0 | 84 | U | 10 | 14 | U | 2 | 7 | U | 10 | 21 |
| 2A | S | 0 | 84 | U | 6 | 7 | U | 2 | 21 | U | 6 | 14 |
| 2B | S | 0 | 84 | U | 10 | 7 | U | 2 | 7 | U | 2 | 91 |
| 2C | S | 0 | 70 | U | 10 | 7 | U | 4 | 7 | U | 4 | 7 |
| 3A | S | 0 | 84 | S, LV | 0 | 8 | S | 0 | 77 | U | 2 | 56 |
| 3B | S | 0 | 84 | U | 10 | 1 | U | 10 | 1 | U | 10 | 14 |
| 4A | S | 0 | 84 | U | 10 | 1 | U | 10 | 1 | U | 10 | 1 |

TABLE 1-continued

| | | | | | | | | | | | | |
|---|---|---|---|---|---|---|---|---|---|---|---|---|
| 4B | S | 0 | 84 | U | 10 | 14 | NT | | | U | 10 | 7 |
| 5 | S | 0 | 70 | U | 10 | 14 | NT | | | U | 5 | 21 |
| 6 | S | 0 | 84 | U | 10 | 1 | U | 10 | 7 | U | 5 | 7 |
| 7 | S | 0 | 84 | NT | | | NT | | | U, PR | — | 14 |

Key:
STAB = Stable/Unstable Rating
S = Stable
U = Unstable
LV = Low Viscosity (initial)
NT = Not Tested
PR = Poor rheology and texture
SEP = Phase Separation Rating Scale

| Numerical Rating | Visual Separation | Stability Interpretation |
|---|---|---|
| 0 | No Separation | Stable |
| 1 | Creaming | Borderline Unstable |
| 2 | Separation (0.1–0.2 cm) | Unstable |
| 5 | Separation (0.5 cm) | Unstable |
| 10 | Separation (4+ cm) | Unstable |

DAY = Number of days at 45° C.

As apparent from the data presented in Table 1, the rheology modifying polymer of the present invention (Sample A of each example) yielded improved stability with regard to Examples 1 through 7, whereas the absence of a polymer or the utilization of either polymer X and Y did not yield a stabilized system.

"Back-Acid" Thickening Data

Select example formulations were prepared using the "Back-Acid" formulation technique. The viscosity and yield value measurements were recorded at the initial high pH. Measurements were again recorded after the subsequent addition of the acidic material. Note that the values of viscosity and yield value, as described in Table 2, increase after the acid addition using Polymer W of the present invention. Note that viscosity and yield value do not increase with Polymer X and Polymer Y.

TABLE 2

| Example # | Polymer | Reading | pH | Visosity* (cP) | Yield Value** (dynes/cm²) |
|---|---|---|---|---|---|
| 2B | W | Before Citric Acid addition | 6.2 | 1,800 | 20 |
| | | After Citric Acid addition | 5.5 | 7,400 | 160 |
| 3A | W | Before Citric Acid addition | 6.5 | 3,300 | 22 |
| | | After Citric Acid addition | 5.0 | 7,800 | 180 |
| | X | Before Citric Acid addition | 6.5 | 11,000 | 28 |
| | | After Citric Acid addition | 5.2 | 700 | 28 |
| 9 | W | Before Citric Acid addition | 6.5 | 4,600 | 270 |
| | | After Citric Acid addition | 4.5 | 5,500 | 440 |
| | X | Before Citric Acid addition | 6.5 | 11,000 | 100 |
| | | After Citric Acid addition | 4.5 | 700 | 25 |
| | Y | Before Citric Acid addition | 6.5 | 6,000 | 300 |
| | | After Citric Acid addition | 4.5 | 2,900 | 100 |
| 13 | W | Before Citric Acid addition | 7.8 | 6,500 | 520 |
| | | After Citric Acid addition | 6.8 | 11,300 | 1,380 |
| 14 | W | Before Citric Acid addition | 7.0 | 1,825 | 25 |
| | | After Citric Acid addition | 5.0 | 4,550 | 170 |

*Brookfield Viscosity @ 20 rpm, Spindle 4
**Brookfield Yield Value @ 1 and 0.5 rpm Improved Pearlescent Appearance The following formulations were rated according to their pearlescent appearance. The formulas were observed initially (immediately after making), and again after one week of stability testing in 45° C. oven. Formulas with the polymer of the present invention (Polymer W) provided an improved pearlescent appearance compared to other polymers (Polymers X and Y) and further maintain this appearance on stability.

TABLE 3

Rating of Pearlescent Appearance of Example Formulations

| Example # | Initial Rating | | | | Rating After One Week Aging @ 45° C. | | | |
|---|---|---|---|---|---|---|---|---|
| Polymer | W | None | X | Y | W | None | X | Y |
| 2A | 9 | 9 | 9 | 2 | 9 | 1 | 1 | 0 |
| 2B | 8 | 8 | 8 | 1 | 8 | 0 | 0 | 0 |
| 2C | 10 | 10 | 10 | 3 | 10 | 0 | 0 | 0 |
| 3B | 10 | 9 | 9 | 5 | 10 | 0 | 0 | 0 |
| 4B | 10 | 10 | NT | 6 | 0 | 0 | NT | 0 |

TABLE 3-continued

Rating of Pearlescent Appearance of Example Formulations

| Example # | Initial Rating | | | | Rating After One Week Aging @ 45° C. | | | |
|---|---|---|---|---|---|---|---|---|
| Polymer | W | None | X | Y | W | None | X | Y |

Key
NT = Not Tested

Rating Scale for Pearlescent Appearance

| Rating | Description |
|---|---|
| 10 | Extremely pearlescent appearance. Very intense and vibrant, satiny, elegant, shiny and lustrous. |
| 9 | |
| 8 | Good pearlescent appearance. |
| 7 | |
| 6 | |
| 5 | Medium pearlescent appearance. Not intense or lustrous. |
| 4 | |
| 3 | Slightly pearlescent appearance. |
| 2 | |
| 1 | |
| 0 | No pearlescent appearance. Completely opaque and flat |

Photographs of the comparative stability testing of select formulations as shown in data Table I are set forth in the various Figures.

| Sample | Polymer Code | Description |
|---|---|---|
| A | "W" | Acrylates Crosspolymer (present invention) |
| B | | No Polymer |
| C | "X" | Acrylates/Ceteth-20 Methacrylate Copolymer |
| D | "Y" | Acrylates/C10–30 Alkyl Acrylate Crosspolymer |

FIG. 1 relates to Example 2A (pearlized 2-in-1 conditioning shampoo) stability testing at 45° C. for 10 weeks. This photo demonstrates the stability of sample A, and creaming instability of samples B, C, and D. Note that the pearlescent appearance is also diminished in samples B, C, and D.

Figure 2:
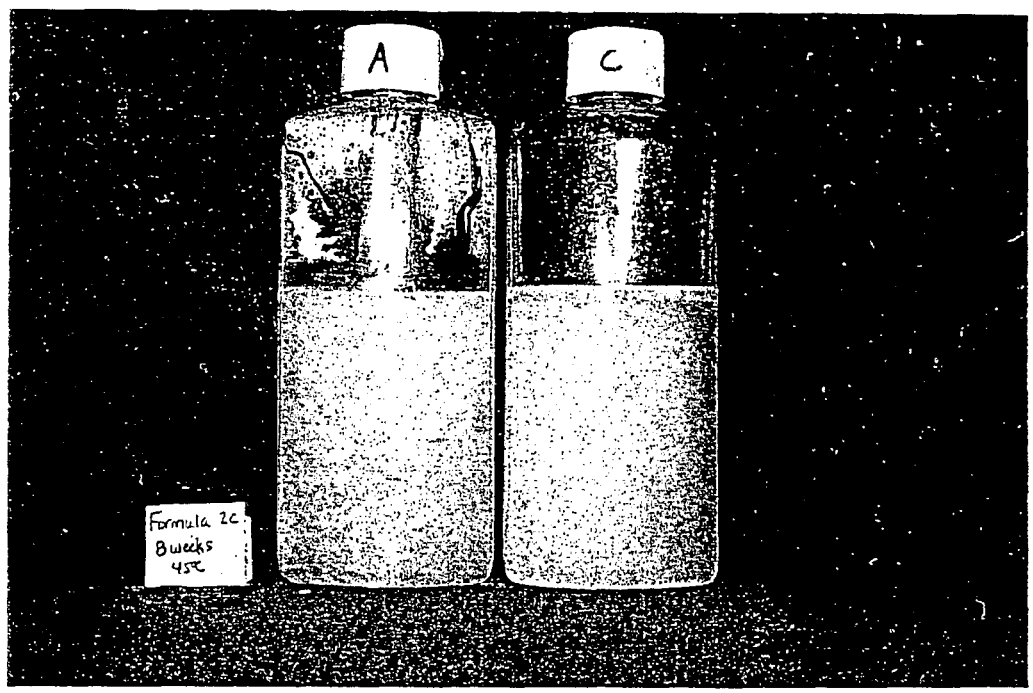
FIG. 2 is a photograph of containers of Example 2C (pearlized 2-in-1 conditioning shampoo with mica) showing stability testing at 45° C. for 8 weeks.

FIG. 2 relates to Example 2C (pearlized 2-in-1 conditioning shampoo with mica) stability testing at 45° C. for 8 weeks. This photo demonstates the enhanced pearlescent appearance and stability of sample A. Creaming instability and a dull appearance are observed in sample C.

Figure 3:
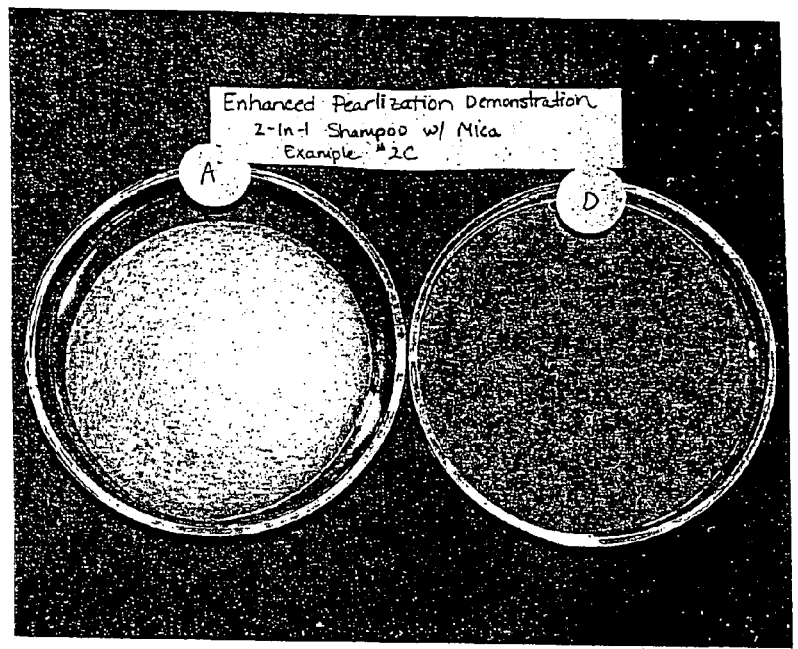
FIG. 3 is a photograph of containers of Example 2C (pearlized 2-in-1 conditioning shampoo with mica) showing the initial appearance.

FIG. 3 relates to Example 2C (pearlized 2-in-1 conditioning shampoo with mica) pearlescent appearance. Note the brilliant appearance of sample A (rating 10), and dull, flat appearance of sample D (rating 0).

Figure 4:
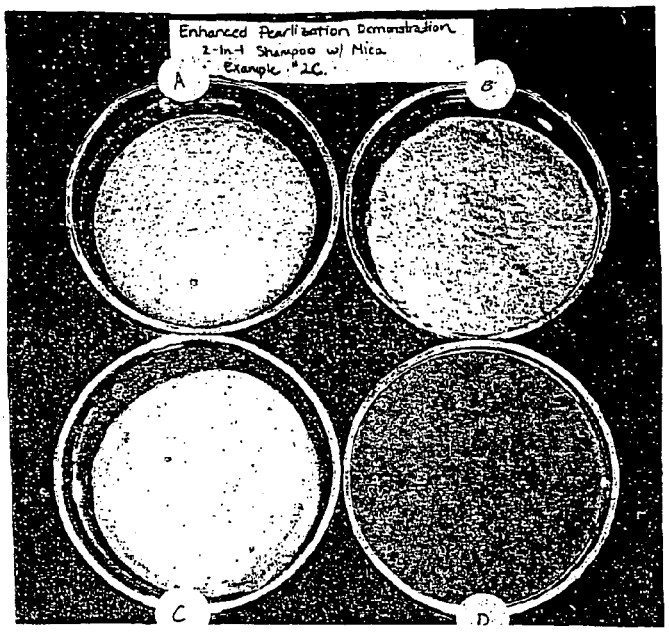
FIG. 4 is a photograph of containers of Example 2C (pearlized 2-in-1 conditioning shampoo in mica) showing the initial appearance (top) and after 12 hours (bottom)
Figure 4:
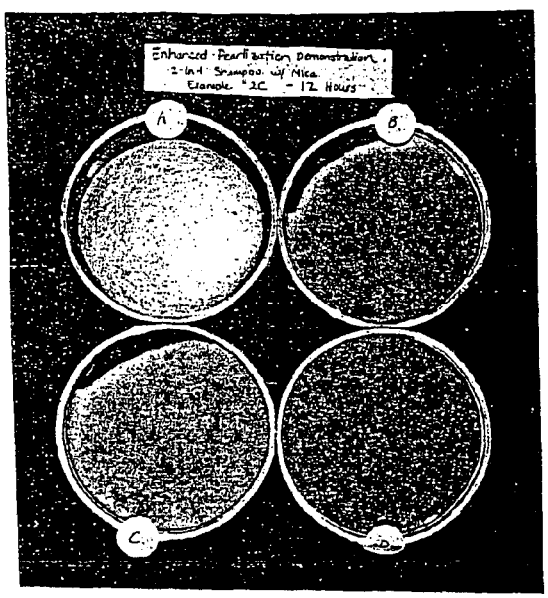

FIG. 4 relates to Example 2C (pearlized 2-in-1 conditioning shampoo with mica) pearlescent appearance. Top photo is initial appearance, bottom photo is after 12 hours. Note the dull appearance of samples B, C, and D after 12 hours. Sample A maintains brilliant pearlescent appearance.

Figure 5:
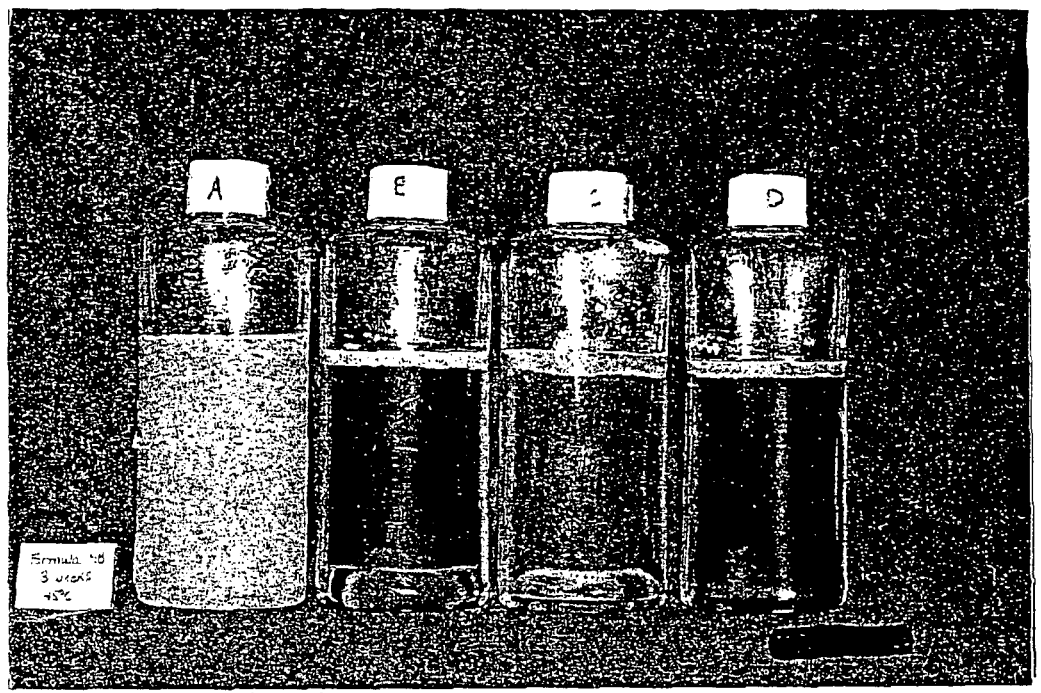
FIG. 5 is a photograph of containers of Example 4A (salicylic acid facial scrub) showing stability testing at 45° C. for 8 weeks.

FIG. 5 relates to Example 4A (salicylic acid facial scrub) stability testing at 45° C. for 8 weeks. This photo demonstrates the stability and suspension of jojoba beads in sample A. Extreme instability and separation of the jojoba beads is observed in samples B, C, and D.

Figure 6:
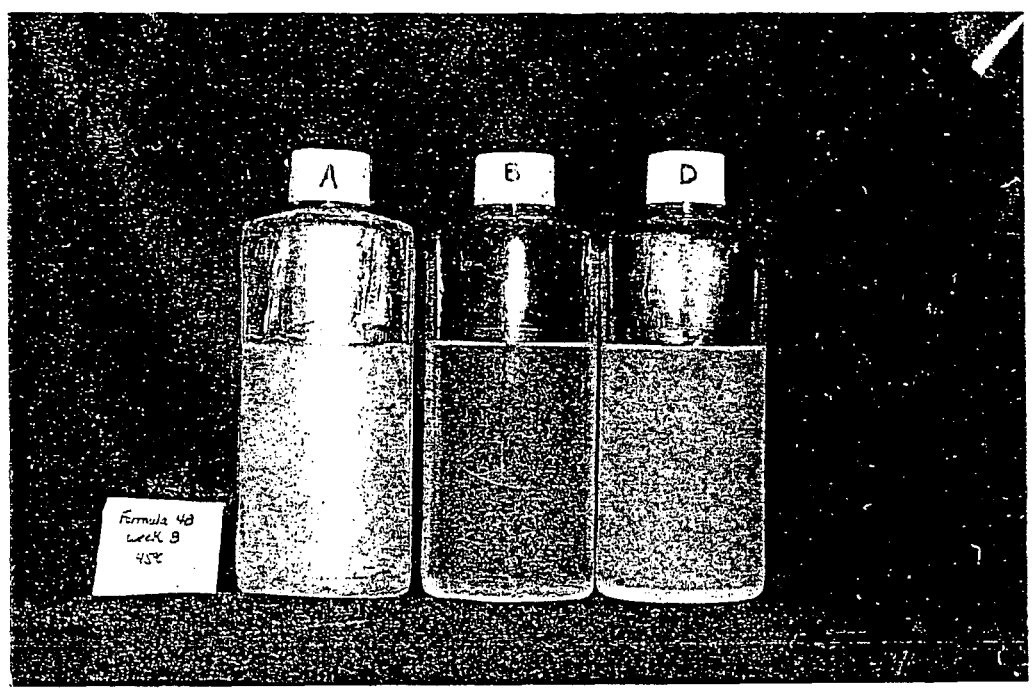
FIG. 6 is a photograph of containers of Example 4B (salicylic acid shampoo with mica) showing stability testing at 45° C. for 8 weeks.

FIG. 6 relates to Example 4B (salicylic acid shampoo with mica) stability testing at 45° C. for 8 weeks. This photo demonstrates the stability of sample A, as well as an enhanced pearlescent appearance. Extreme instability and sedimentation of mica is observed in samples B and D.

Figure 7:
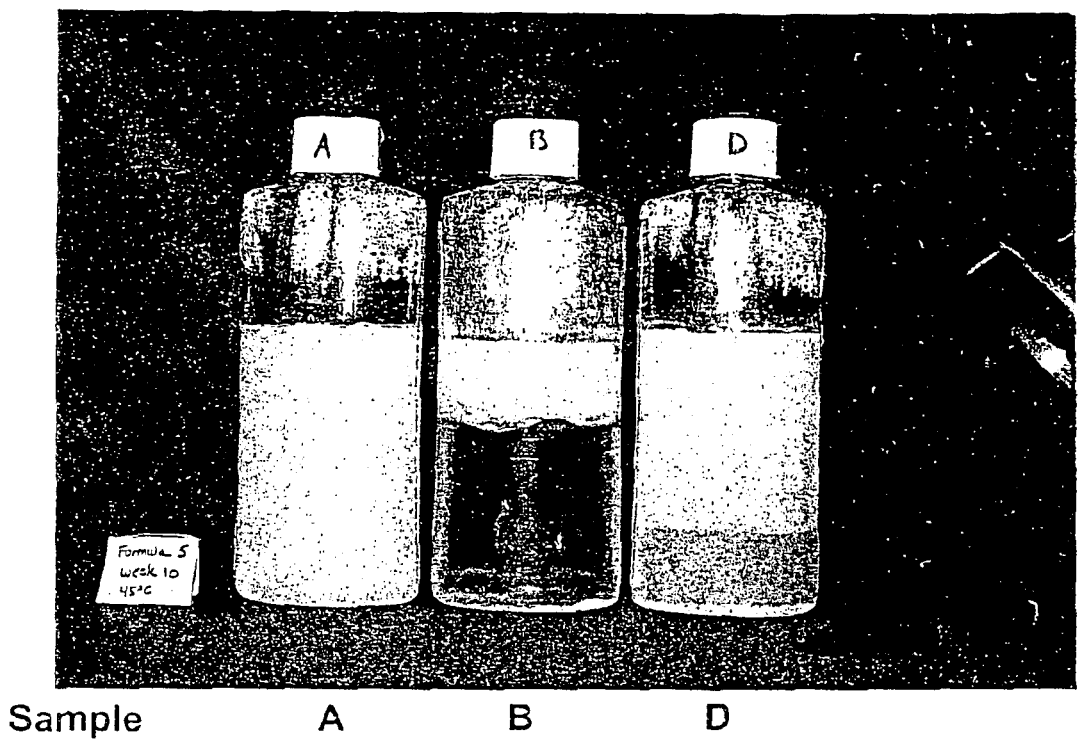
FIG. 7 is a photograph of containers of Example 5 (pearlized mild body wash) showing stability testing at 45° C. for 10 weeks.

FIG. 7 relates to Example 5 (pearlized mild body wash) stability testing at 45° C. for 10 weeks. This photo demonstrates the stability of sample A, and vivid phase separation (instability) and sedimentation of samples B and D.

Figure 8:
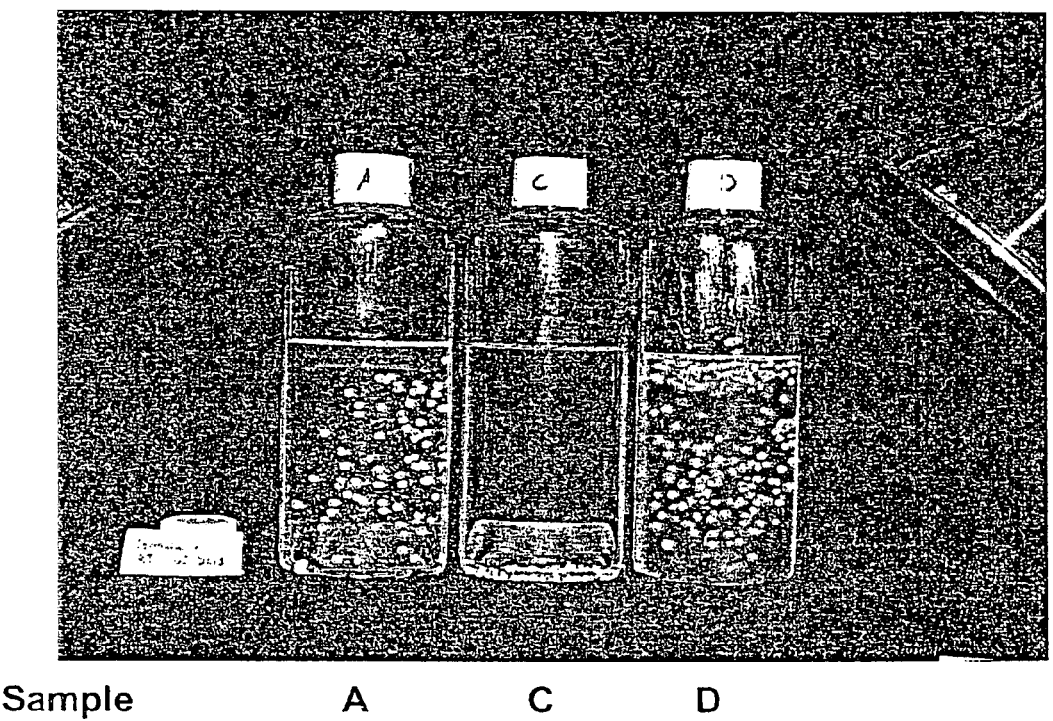
FIG. 8 is a photograph of containers of Example 6 (clear bath gel with suspended beads) showing stability testing at room temperature for 8 weeks.

FIG. 8 relates to Example 6 (clear bath gel with suspended beads) stability testing at room temperature for 8 weeks. This photo demonstrates the stability and suspension of beads in sample A. Instability and separation of the beads is observed in sample C and D.

While in accordance with the Patent Statutes the best mode and preferred embodiment have been set forth, the scope of the invention is not limited thereto but rather by the scope of the claims.

What is claimed is:

1. A stable, aqueous surfactant containing composition, comprising:
  a. at least one anionic, zwitterionic, amphoteric, nonionic, or cationic surfactant, or combinations thereof;
  b. at least one substantially crosslinked alkali-swellable acrylate copolymer rheology modifier;
  c. water;
  d. an effective amount of at least one alkaline material to yield a composition having a pH of from about 5 to about 14; and
  e. an effective amount of a subsequently added acidic material to yield a composition having a reduced pH of from about 1 to about 12; wherein said at least one crosslinked alkali-swellable acrylate copolymer comprises:
  f. about 20% to about 80% by weight of at least one carboxylic acid monomer comprising acrylic acid, methacrylic acid, itaconic acid, fumaric acid, crotonic acid, aconitic acid, or maleic acid, or combinations thereof;
  g. about 80% to about 15% by weight of at least one α,β-ethylenically unsaturated monomer, wherein said monomer has the formula:

$$CH_2=CXY, \quad \text{i)}$$

where X is H and Y is —COOR, —C$_6$H$_4$R', —CN, —CONH$_2$, —Cl, —NC$_4$H$_6$O, NH(CH$_2$)$_3$COOH, —NHCOCH$_3$, —CONHC(CH$_3$)$_3$, —CO—N(CH$_3$)$_2$,
  or X is CH$_3$ and Y is —COOR, —C$_6$H$_4$R', —CN;
  or —CH=CH$_2$;
  or X is Cl and Y is Cl, and R is C$_1$–C$_{18}$ alkyl, or hydroxy C$_2$–C$_{18}$ alkyl,
  R' is H or C$_1$–C$_{18}$ alkyl,
  or having the formula:

$$CH_2=CH \, (OCOR^1); \quad \text{ii)}$$

where R$^1$ is C$_1$–C$_{18}$ alkyl;
  or having the formula:

$$CH_2=CH_2 \text{ or } CH_2=CHCH_3; \quad \text{iii)}$$

h. from about 0.01 to about 5% by weight of at least one polyunsaturated compound useful in forming a partially or substantially crosslinked three dimensional network; and
  i. at least one substantially insoluble material requiring suspension or stabilization.

2. A composition according to claim 1, wherein said substantially insoluble material includes pumice; calcium carbonate; talc; potato starch; tapioca starch; jojoba beads; polyethylene beads; walnut shells; loofah; apricot seeds; almond meal; corn meal; paraffin; oat bran/oat hulls; gelatin beads; alginate beads; stainless steel fibers; iron oxide pigments; air bubbles; mica coated iron oxides; kaolin clay; zinc pyrithione; salicylic acid; zinc oxide; zeolite; styrofoam beads; phosphates; silica, and the like, teatree powder, microsponges, Confetti®, talc, beeswax, and combinations thereof.

3. A composition according to claim 1, wherein the amount of the said copolymer is from about 0.1% to about 10% by weight based upon the total weight of said stable composition, and wherein the amount of said surfactant is from about 1% to about 80% by weight based upon the total weight of said stable composition.

4. A composition according to claim 3, wherein said acidic material is citric acid, acetic acid, beta-hydroxy acid, salicylic acid, alpha-hydroxy acid, lactic acid, glycolic acid, hydrochloric acid, sulfuric acid, nitric acid, sulfamiic acid, phosphoric acid, or natural fruit acids, or combinations thereof.

5. A composition according to claim 4, wherein the said copolymer is derived from:
   a. about 35% to about 65% by weight of acrylic acid or methacrylic acid, or combinations thereof,
   b. about 65% to about 35% by weight of ethylacrylate, or methylacrylate, or combinations thereof, and
   c. about 0.03% to about 3% by weight of polyalkenyl ethers of sucrose or polyalcohols; or trimethylolpropane tri(meth)acrylate, glycidyl methacrylate, N-methylolacrylamide, or combinations thereof.

6. A composition according to claim 1, wherein said substantially insoluble material is a "biologically active" material having pharmaceutical, veterinary, biocidal, herbicidal, pesticidal, or other biological activity.

7. A composition according to claim 1, wherein said substantially insoluble material is a silicone, or an oily material, or a pearlescent material, or combinations thereof.

8. A composition according to claim 7, wherein said insoluble silicone is polydimethylsiloxane, amodimethicone, amodimethicone macroemulsion or microemulsion, dimethicone, dimethiconol (silicone gum), cyclomethicone, phenyltrimethicone, a dimethicone or dimethiconol microemulsion or macroemulsion, an organo polysiloxane, alkoxysilicone, or any combination thereof, wherein the amount of said silicone is from about 0.1 to about 20% by weight based upon the total weight of said stable composition.

9. A composition according to claim 7, wherein said insoluble pearlescent material is titanium dioxide coated mica, iron oxide coated mica, ethylene glycol monostearate, ethylene glycol distearate, polyethylene glycol distearate, bismuth oxychloride coated mica, myristyl myristate, guanine (fish scales), or glitter (polyester or metallic), or combinations thereof, wherein the amount of said pearlescent material is from about 0.05% to about 10% by weight based upon the total weight of said stable composition.

10. A composition according to claim 8, wherein said composition is substantially free of a fatty acid, a fatty acid ester, a fatty alcohol, or combinations thereof.

11. A composition according to claim 5, wherein said composition is a personal care cleansing composition, wherein said acid is salicylic acid or alpha-hydroxy acid, and wherein the amount of said acid is from about 0.2 to about 6% by weight.

12. A composition according to claim 5, wherein said composition is a personal care emulsion composition, wherein said acid is an alpha-hydroxy acid or beta-hydroxy acid, and wherein the amount of said acid is from about 0.2% to about 15% by weight.

13. A composition according to claim 2, wherein said composition is an anti-dandruff shampoo, wherein said substantially insoluble material requiring suspension or stabilization is zinc pyrithione, and wherein the amount of said zinc pyrithione is from about 0.1% to 5% by weight.

\* \* \* \* \*